(12) United States Patent
Tsukagoshi et al.

(10) Patent No.: US 10,110,874 B2
(45) Date of Patent: Oct. 23, 2018

(54) MEDICAL-IMAGE PROCESSING APPARATUS GENERATING PLURAL PARALLAX IMAGES WITH DIFFERENT VIEWPOINT POSITIONS BASED ON ADJUSTING PARALLACTIC ANGLES

(71) Applicant: TOSHIBA MEDICAL SYSTEMS CORPORATION, Otawara-Shi (JP)

(72) Inventors: Shinsuke Tsukagoshi, Nasushiobara (JP); Takashi Tsutsumi, Utsunomiya (JP); Kenji Fujii, Nasushiobara (JP)

(73) Assignee: Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 14/953,164

(22) Filed: Nov. 27, 2015

(65) Prior Publication Data

US 2016/0080719 A1    Mar. 17, 2016

Related U.S. Application Data

(63) Continuation of application No. PCT/JP2014/064174, filed on May 28, 2014.

(30) Foreign Application Priority Data

May 28, 2013  (JP) .................................. 2013-112386

(51) Int. Cl.
  *G06K 9/00*  (2006.01)
  *H04N 13/128*  (2018.01)
  (Continued)

(52) U.S. Cl.
  CPC ......... *H04N 13/128* (2018.05); *G06F 19/321* (2013.01); *G06T 1/20* (2013.01);
  (Continued)

(58) Field of Classification Search
  CPC ......... G06F 19/321; G06T 1/20; G06T 15/08; H04N 13/0011; H04N 13/0022;
  (Continued)

(56) References Cited

U.S. PATENT DOCUMENTS 7,567,648 B2 * 7/2009 Tsubaki ................. A61B 6/022
                                                     378/41
7,834,903 B2   11/2010 Saishu et al.
(Continued)

FOREIGN PATENT DOCUMENTS

JP    2000-030044     1/2000
JP    2000-139901     5/2000
(Continued)

OTHER PUBLICATIONS

International Search Report dated Sep. 2, 2014 in PCT/JP2014/064174 filed May 28, 2014 (with English translation).
(Continued)

*Primary Examiner* — Amara Abdi
(74) *Attorney, Agent, or Firm* — Oblon, McClelland, Maier & Neustadt, L.L.P.

(57) ABSTRACT

A medical-image processing apparatus according to an embodiment includes a reconstructing circuitry and a display control circuitry. The reconstructing circuitry performs a volume rendering operation on volume data while moving the viewpoint position by a predetermined parallactic angle, and generates a parallax image group that includes a plurality of parallax images with different viewpoint positions. The display control circuitry causes a stereoscopic display monitor to display the parallax image group as a stereoscopic image. With regard to the volume data that is acquired by each of the multiple types of medical-image diagnostic apparatus, the reconstructing circuitry adjusts each parallactic angle during generation of the parallax
(Continued)

image group and, in accordance with each of the adjusted parallactic angles, generates each parallax image group on the basis of the volume data that is acquired by each of the multiple types of medical-image diagnostic apparatus.

17 Claims, 20 Drawing Sheets

(51) Int. Cl.

| | | |
|---|---|---|
| H04N 13/111 | (2018.01) | |
| H04N 13/275 | (2018.01) | |
| H04N 13/341 | (2018.01) | |
| G06F 19/00 | (2018.01) | |
| H04N 13/00 | (2018.01) | |
| H04N 13/02 | (2006.01) | |
| H04N 13/04 | (2006.01) | |
| G06T 1/20 | (2006.01) | |
| G06T 15/08 | (2011.01) | |
| G01R 33/28 | (2006.01) | |

(52) U.S. Cl.
CPC .......... *G06T 15/08* (2013.01); *H04N 13/0011* (2013.01); *H04N 13/0275* (2013.01); *H04N 13/0447* (2013.01); *H04N 13/111* (2018.05); *H04N 13/275* (2018.05); *H04N 13/341* (2018.05); *G01R 33/283* (2013.01)

(58) Field of Classification Search
CPC .......... H04N 13/0275; H04N 13/0438; H04N 13/0447; H04N 13/0495; G01R 33/283
See application file for complete search history.

(56) References Cited

U.S. PATENT DOCUMENTS

| | | | |
|---|---|---|---|
| 2007/0098299 | A1 | 5/2007 | Matsumoto |
| 2008/0298660 | A1 | 12/2008 | Yamagata |
| 2010/0085173 | A1* | 4/2010 | Yang ..................... G08G 1/017 340/435 |
| 2010/0238277 | A1* | 9/2010 | Takahashi ................ G02B 3/14 348/59 |
| 2011/0122234 | A1* | 5/2011 | Kikkawa .................. G06T 7/97 348/51 |
| 2011/0235066 | A1* | 9/2011 | Sakuragi ................ G06T 15/00 358/1.6 |
| 2012/0069954 | A1* | 3/2012 | Iso .......................... A61B 6/03 378/7 |
| 2012/0320043 | A1* | 12/2012 | Tsukagoshi .......... H04N 13/111 345/419 |
| 2012/0320167 | A1* | 12/2012 | Tsukagoshi ........ H04N 13/0062 348/51 |
| 2012/0327198 | A1* | 12/2012 | Tsukagoshi ........ H04N 13/0011 348/51 |
| 2013/0021335 | A1* | 1/2013 | Arakita .................... G02B 3/14 345/419 |
| 2013/0176404 | A1* | 7/2013 | Tsukagoshi .......... H04N 13/007 348/51 |
| 2014/0035910 | A1* | 2/2014 | Wakai ..................... A61B 5/055 345/419 |
| 2014/0340400 | A1* | 11/2014 | Takeguchi ............ G06F 3/0304 345/424 |

FOREIGN PATENT DOCUMENTS

| | | | | |
|---|---|---|---|---|
| JP | 2005-086414 | | 3/2005 | |
| JP | 2006-033851 | | 2/2006 | |
| JP | 2007-014706 | | 1/2007 | |
| JP | 2008-113800 | * | 5/2008 | ............... A61B 8/00 |
| JP | 2008-188417 | | 8/2008 | |
| JP | 2012-217633 | | 11/2012 | |
| JP | 2012-221290 | * | 11/2012 | ............... A61B 6/03 |
| JP | 2012-249676 | | 12/2012 | |

OTHER PUBLICATIONS

Written Opinion dated Sep. 2, 2014 in PCT/JP2014/064174 filed May 28, 2014.

\* cited by examiner

FIG.11
(A)
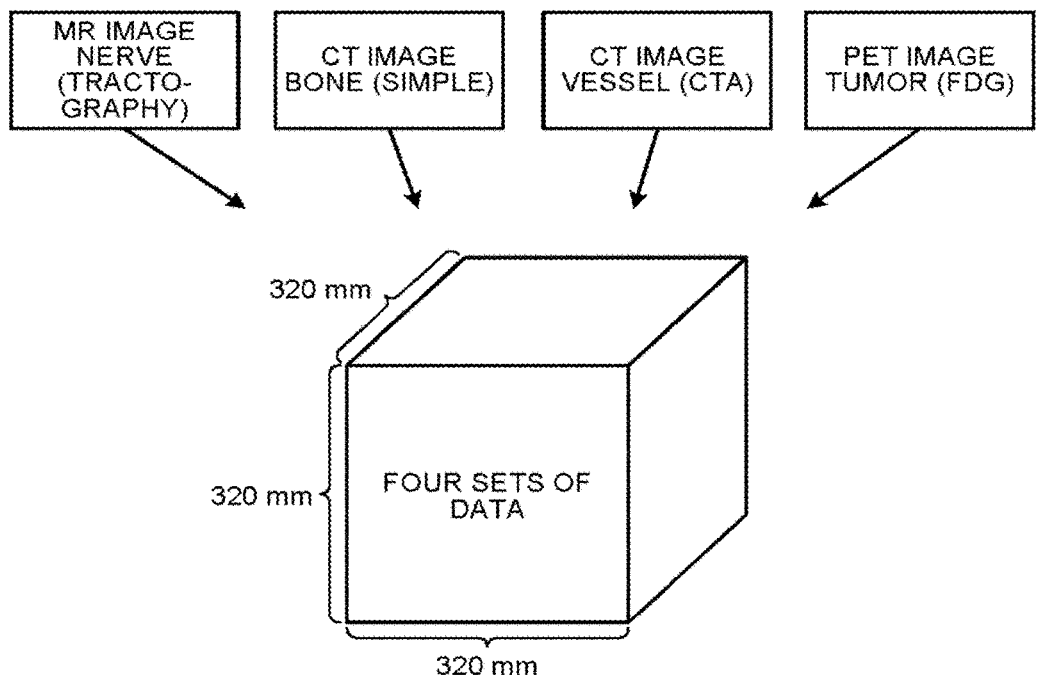
(B)
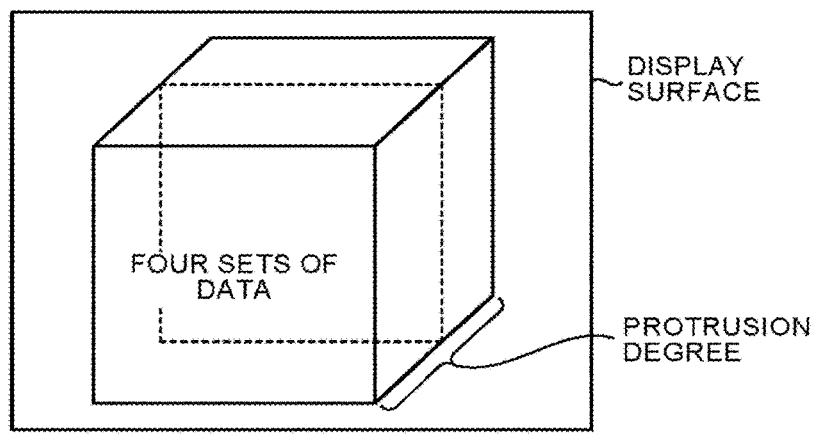

FIG.12
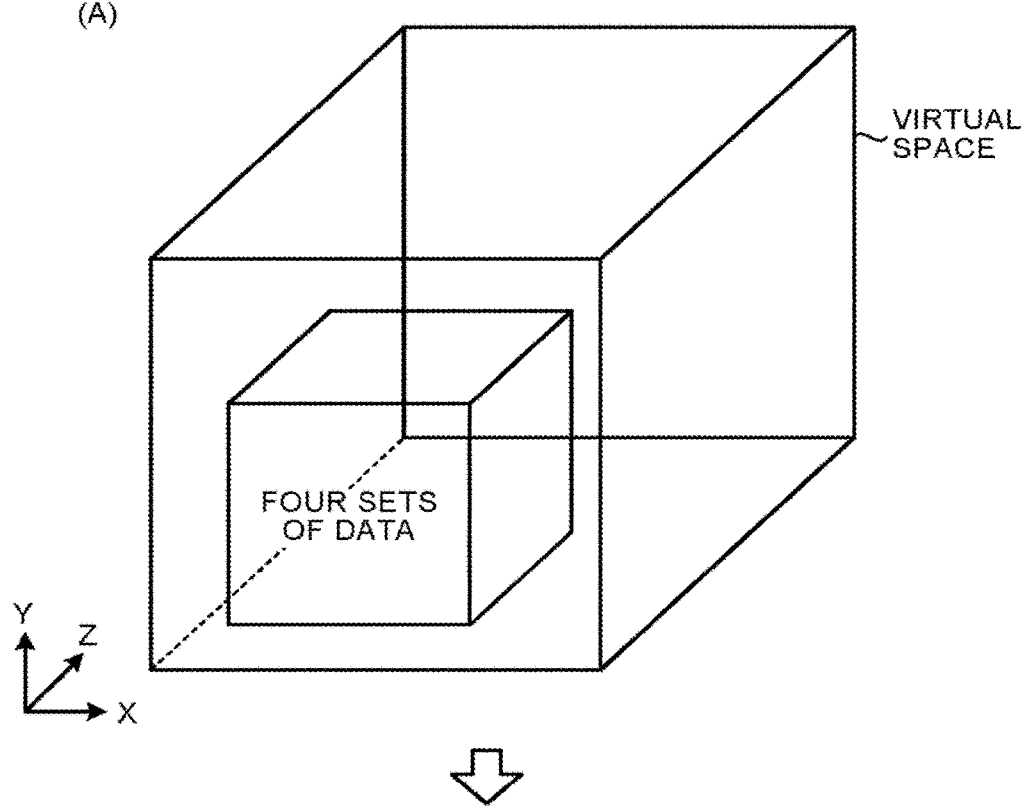
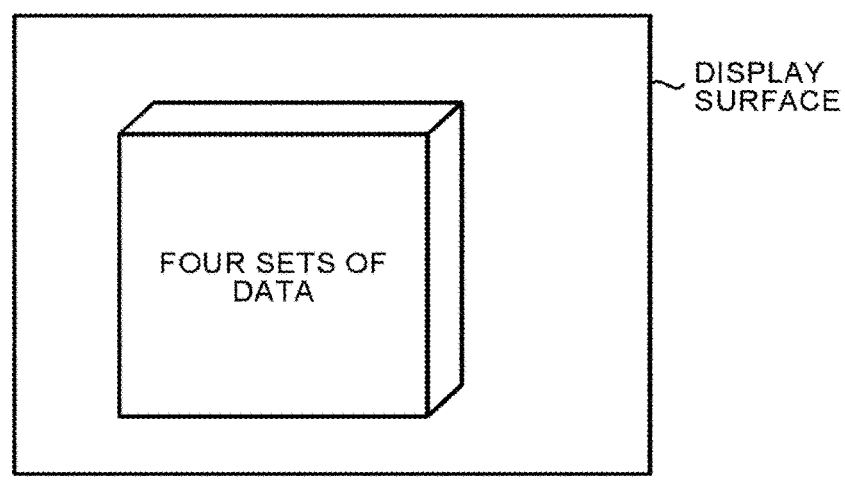

FIG.13
(A)
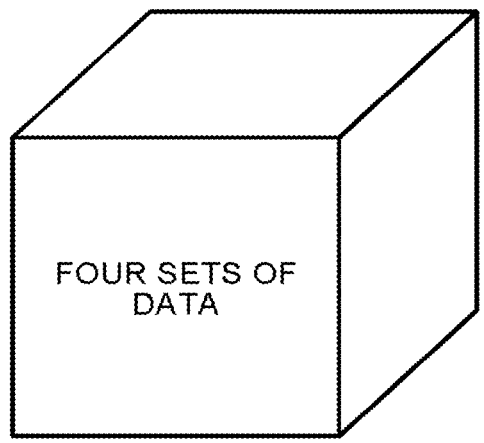
(B)
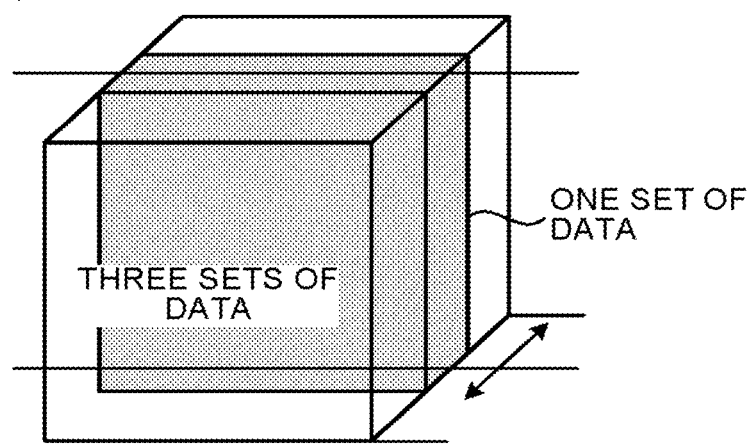

FIG.14
(A)
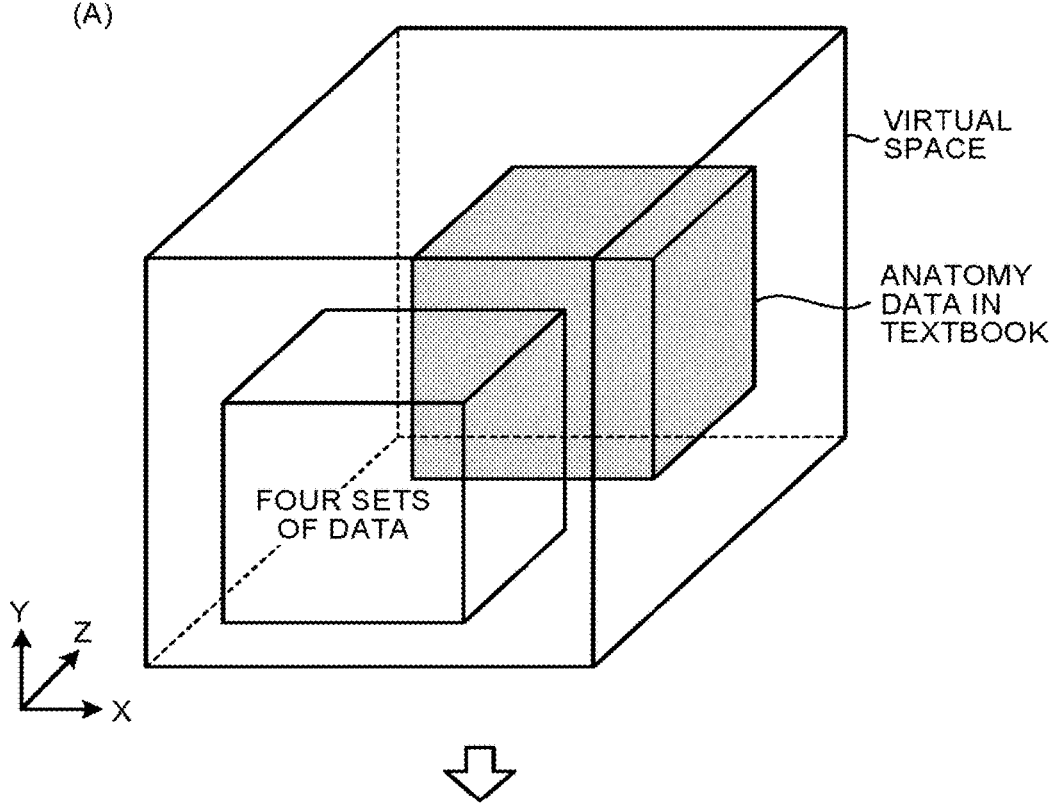
(B)
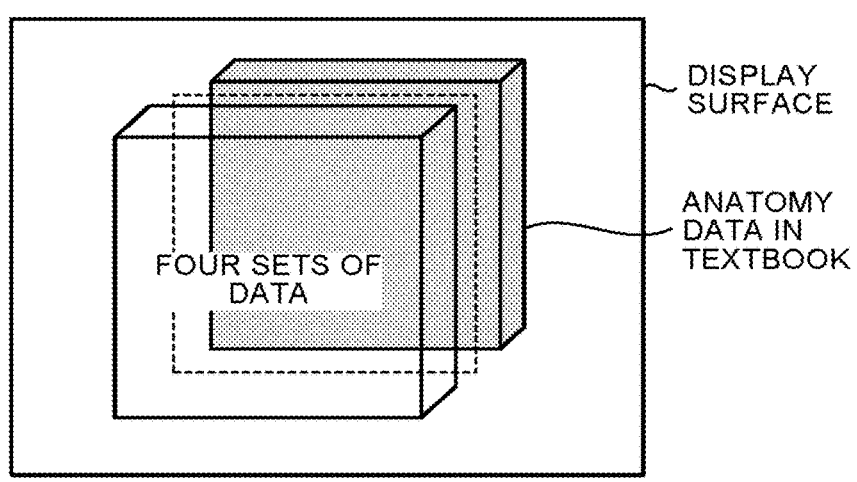

FIG.18

| SIZE | SENSE OF DEPTH |
|---|---|
| XY < 1.2Z | 1 : 1 : 0.8 |
| XY < 1.5Z | 1 : 1 : 0.5 |
| XY < 2.0Z | 1 : 1 : 0.25 |

FIG.20A

| MODALITY | TYPE | AREA | | PROTRUSION DEGREE |
|---|---|---|---|---|
| | | AP | RL | |
| CT | HEAD CTA | 100% | 100% | 100% |
| | . | . | . | . |
| | . | . | . | . |
| | . | . | . | . |
| | CHEST SIMPLE | 50% | 100% | 100% |
| | CHEST ONE LUNG | 100% | 100% | 100% |
| | . | . | . | . |
| | . | . | . | . |
| | . | . | . | . |
| MRI | HEAD MRA | 75% | 75% | 75% |
| | HEAD NERVE | 75% | 75% | 75% |
| | . | . | . | . |
| | . | . | . | . |
| | . | . | . | . |
| NUCLEAR | WHOLE BODY FDG | 50% | 75% | 75% |
| | HEAD SPECT | 50% | 50% | 100% |
| | . | . | . | . |
| | . | . | . | . |
| | . | . | . | . |
| . | . | . | . | . |
| | . | . | . | . |

FIG.20B

| | PROTRUSION DEGREE | PARALLACTIC ANGLE |
|---|---|---|
| 512×512 | 100% | 0.4 DEGREES |
| | 50% | 0.3 DEGREES |
| | 25% | 0.2 DEGREES |
| | . | . |
| | PROTRUSION DEGREE | PARALLACTIC ANGLE |
| 256×256 | 100% | 0.2 DEGREES |
| | 50% | 0.15 DEGREES |
| | 25% | 0.1 DEGREES |
| | . | . |
| | PROTRUSION DEGREE | PARALLACTIC ANGLE |
| 160×160 | 75% | 0.15 DEGREES |
| | 50% | 0.1 DEGREES |
| | 25% | 0.08 DEGREES |
| | . | . |
| . | . | . |
| | . | . |

MEDICAL-IMAGE PROCESSING APPARATUS GENERATING PLURAL PARALLAX IMAGES WITH DIFFERENT VIEWPOINT POSITIONS BASED ON ADJUSTING PARALLACTIC ANGLES

CROSS-REFERENCE TO RELATED APPLICATIONS

This application is a continuation of PCT international application Ser. No. PCT/JP2014/064174 filed on May 28, 2014 which designates the United States, incorporated herein by reference, and which claims the benefit of priority from Japanese Patent Application No. 2013-112386, filed on May 28, 2013, the entire contents of which are incorporated herein by reference. The entire contents of the prior Japanese Patent Application No. 2014-110561, filed on May 28, 2014, are also incorporated herein by reference.

FIELD

Embodiments described herein relate generally to a medical-image processing apparatus.

BACKGROUND

Conventionally, the monitors have been put into practical use, with which 2-parallax images, captured from two viewpoints, are stereoscopically viewable by using a dedicated device, such as stereoscopic glasses. Furthermore, the monitors have been put into practical use in recent years, with which multi-parallax images (e.g., 9-parallax images), captured from multiple viewpoints, are stereoscopically viewable with the naked eye by using a light beam controller, such as a lenticular lens. Here, 2-parallax images or 9-parallax images, displayed on the stereoscopic monitor, are sometimes generated by estimating the depth information on the image that is captured from a single viewpoint and by image processing using the estimated information.

Furthermore, as for medical-image diagnostic apparatus, such as X-ray CT (Computed Tomography) apparatus, MRI (Magnetic Resonance Imaging) apparatus, or ultrasonic diagnostic apparatus, the apparatus that are capable of generating three-dimensional medical image data (hereinafter, volume data) have been put into practical use. Conventionally, the volume data, generated by the medical-image diagnostic apparatus, is two-dimensional images due to various types of image processing, and they are displayed on the general-purpose monitor in two dimensions. For example, the volume data, generated by the medical-image diagnostic apparatus, is two-dimensional images to which three-dimensional information is applied due to a volume rendering operation, and they are displayed on the general-purpose monitor in two dimensions. However, according to the conventional technologies, it is sometimes difficult to display easily observable medical images in a stable manner.
Cited references

BRIEF DESCRIPTION OF THE DRAWINGS

FIG. 11 is a diagram that illustrates an example of the fusion of the stereoscopic image according to the first embodiment;

FIG. 12 is a diagram that illustrates an example of the operation to change the protrusion position by reconstructing circuitry according to the first embodiment;

FIG. 13 is a diagram that illustrates an example of the control by the workstation according to the first embodiment;

FIG. 14 is a diagram that illustrates an example of the stereoscopic image according to the first embodiment;

FIG. 18 is a diagram that illustrates an example of the adjustment information in the depth direction, which is referred to by the reconstructing circuitry according to a third embodiment;

FIG. 20A is a diagram that illustrates an example of the information that is stored in storage circuitry according to a fourth embodiment; and FIG. 20B is a diagram that illustrates an example of the information that is stored in the storage circuitry according to the fourth embodiment.

DETAILED DESCRIPTION

According to an embodiment, a medical-image processing apparatus includes processing circuitry. The processing circuitry is configured to perform a volume rendering process on volume data while moving a viewpoint position by a predetermined parallactic angle, thereby generating a parallax image group that includes a plurality of parallax images with the different viewpoint positions. The processing circuitry is configured to display the parallax image group as a stereoscopic image on a stereoscopic display monitor. with regard to volume data that is acquired by multiple types of medical-image diagnostic apparatus, the processing circuitry is configured to adjust each of the parallactic angles during generation of the parallax image group and, in accordance with each of the adjusted parallactic angles, generate each parallax image group based on volume data that is acquired by each of the multiple types of the medical-image diagnostic apparatus.

With reference to the attached drawings, a detailed explanation is given below of an embodiment of a medical-image processing apparatus. Furthermore, an explanation is given below of, as an embodiment, an image display system that includes a workstation that functions as a medical-image processing apparatus; however, there may be a case where a medical-image diagnostic apparatus functions as a medical-image processing apparatus or a case where a terminal apparatus functions as a medical-image processing apparatus.

Here, the terms that are used in the following embodiment are explained; "parallax image group" is a group of images that are generated by performing a volume rendering operation on volume data while the viewpoint position is moved by a predetermined parallactic angle. That is, the "parallax image group" is made up of multiple "parallax images" with different "viewpoint positions". Furthermore, "parallactic angle" is the angle that is defined by adjacent viewpoint positions among various viewpoint positions that are set to generate the "parallax image group" and by a predetermined position (e.g., the center of the space) within the space that is represented by the volume data. Furthermore, "parallax number" is the number of "parallax images" that are needed to obtain a stereoscopic view by a stereoscopic display monitor. Furthermore, "9-parallax image", which is described below, is the "parallax image group" that is made up of 9 "parallax images". Moreover, "2-parallax image", which is described below, is the "parallax image group" that is made up of 2 "parallax images".

First Embodiment

Figure 1:
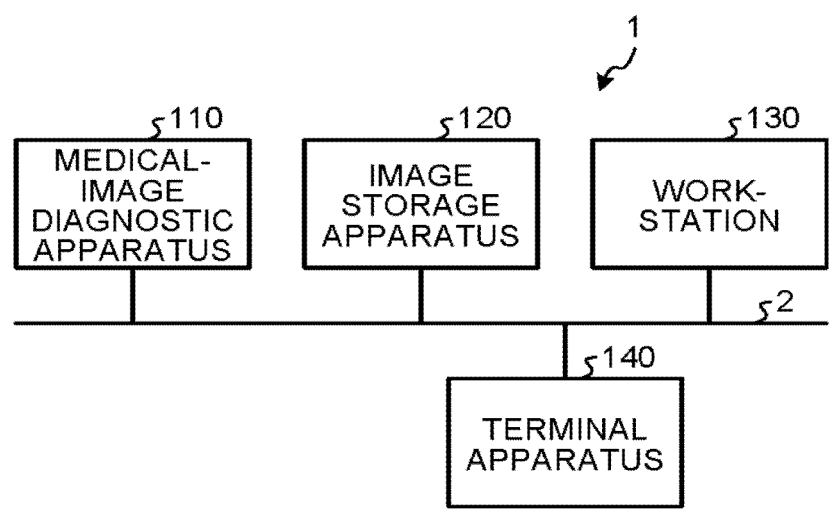
FIG. 1 is a diagram that illustrates an example of the configuration of an image display system according to a first embodiment.

First, an explanation is given of an example of the configuration of an image display system according to a first embodiment. FIG. 1 is a diagram that illustrates an example of the configuration of the image display system according to the first embodiment.

As illustrated in FIG. 1, an image display system 1 according to the first embodiment includes a medical-image diagnostic apparatus 110, an image storage apparatus 120, a workstation 130, and a terminal apparatus 140. The apparatus illustrated in FIG. 1 are in a state such that they can communicate with one another directly or indirectly via, for example, an in-hospital LAN (local area network) 2 that is installed within a hospital. For example, if a PACS (Picture Archiving and Communication System) is introduced into the image display system 1, the apparatus transmit and receive medical images, or the like, to and from one another in accordance with DICOM (Digital Imaging and Communications in Medicine) standard.

The above-described image display system 1 generates a parallax image group by using volume data that is three-dimensional medical image data that is generated by the medical-image diagnostic apparatus 110 and displays the parallax image group on the monitor that allows stereoscopic views, thereby providing stereoscopically viewable medical images to doctors or laboratory technicians who work in the hospital. Specifically, according to the first embodiment, the workstation 130 performs various types of image processing on the volume data and generates the parallax image group. Furthermore, the workstation 130 and the terminal apparatus 140 include a stereoscopically viewable monitor, and the monitor displays the parallax image group that is generated by the workstation 130. Furthermore, the image storage apparatus 120 stores the volume data that is generated by the medical-image diagnostic apparatus 110 and the parallax image group that is generated by the workstation 130. Specifically, the workstation 130 and the terminal apparatus 140 acquire the volume data or the parallax image group from the image storage apparatus 120, process them, and display them on the monitor. Each of the apparatus is sequentially explained below.

The medical-image diagnostic apparatus 110 is an X-ray diagnostic apparatus, an X-ray CT (Computed Tomography) apparatus, an MRI (Magnetic Resonance Imaging) apparatus, an ultrasonic diagnostic apparatus, a SPECT (Single Photon Emission Computed Tomography) apparatus, a PET (Positron Emission computed Tomography) apparatus, a SPECT-CT apparatus where a SPECT apparatus and an X-ray CT apparatus are integrated, a PET-CT apparatus where a PET apparatus and an X-ray CT apparatus are integrated, a group of the above-described apparatus, or the like. Furthermore, the medical-image diagnostic apparatus 110 according to the first embodiment is capable of generating three-dimensional medical image data (volume data).

Specifically, the medical-image diagnostic apparatus 110 according to the first embodiment generates volume data by capturing the subject. For example, the medical-image diagnostic apparatus 110 captures the subject to collect data, such as projection data or MR signals, and uses the collected data to reconstruct medical image data on multiple axial planes along the body-axis direction of the subject, thereby generating volume data. For example, the medical-image diagnostic apparatus 110 reconstructs 500 pieces of axial-plane medical image data. The group of 500 pieces of axial-plane medical image data is the volume data. Furthermore, projection data, MR signals, or the like, on the subject that is captured by the medical-image diagnostic apparatus 110 may be the volume data.

Furthermore, the medical-image diagnostic apparatus 110 according to the first embodiment transmits the generated volume data to the image storage apparatus 120. Furthermore, upon transmitting volume data to the image storage apparatus 120, the medical-image diagnostic apparatus 110 transmits, as supplementary information, for example, the subject ID for identifying a subject, the examination ID for identifying an examination, the apparatus ID for identifying the medical-image diagnostic apparatus 110, or the series ID for identifying a single capturing by the medical-image diagnostic apparatus 110.

The image storage apparatus 120 is the database that stores medical images. Specifically, the image storage apparatus 120 according to the first embodiment stores the volume data, which is transmitted from the medical-image diagnostic apparatus 110, in storage circuitry and holds it. Furthermore, according to the first embodiment, the workstation 130 generates the parallax image group from the volume data and transmits the generated parallax image group to the image storage apparatus 120. Therefore, the image storage apparatus 120 stores the parallax image group, which is transmitted from the workstation 130, in storage circuitry and holds it. Here, according to the present embodiment, there may be a case where the workstation 130 and the image storage apparatus 120, illustrated in FIG. 1, are integrated with each other by using the workstation 130 that is capable of storing large-volume images. That is, according to the present embodiment, there may be a case where the volume data or the parallax image group is stored in the workstation 130 itself.

Furthermore, according to the first embodiment, the volume data and the parallax image group, stored in the image storage apparatus 120, are related to the subject ID, the examination ID, the apparatus ID, the series ID, or the like, while they are stored. Therefore, the workstation 130 or the terminal apparatus 140 conducts searching by using the subject ID, the examination ID, the apparatus ID, the series ID, or the like, thereby acquiring necessary volume data or parallax image group from the image storage apparatus 120.

The workstation 130 is an image processing apparatus that performs image processing on medical images. Specifically, the workstation 130 according to the first embodiment performs various rendering operations on the volume data that is acquired from the image storage apparatus 120 and generates the parallax image group. The parallax image group is a plurality of parallax images that are captured at multiple viewpoints, for example, the parallax image group that is displayed on the monitor, with which 9-parallax images may be stereoscopically viewed with the naked eye, is 9 parallax images with different viewpoint positions.

Furthermore, the workstation 130 according to the first embodiment includes a stereoscopically viewable monitor (hereafter, a stereoscopic display monitor) as a display. The workstation 130 generates a parallax image group and displays the generated parallax image group on the stereoscopic display monitor. As a result, an operator of the workstation 130 may perform an operation to generate a parallax image group while it checks stereoscopically viewable medical images that are displayed on the stereoscopic display monitor.

Furthermore, the workstation 130 transmits the generated parallax image group to the image storage apparatus 120. Here, upon transmitting the parallax image group to the image storage apparatus 120, the workstation 130 transmits, as supplementary information, for example, the subject ID, the examination ID, the apparatus ID, or the series ID. Furthermore, the supplementary information, which is transmitted when the parallax image group is transmitted to the image storage apparatus 120, also includes the supplementary information relating to the parallax image group. The supplementary information relating to the parallax image group includes the number (e.g., "9") of parallax images, the resolution (e.g., "466×350 pixels") of a parallax image, or the like.

The terminal apparatus 140 is a device that allows a doctor or a laboratory technician working in a hospital to view medical images. For example, the terminal apparatus 140 is a PC (Personal Computer), a tablet-type PC, PDA (Personal Digital Assistant), a mobile phone, or the like, which is operated by a doctor or a laboratory technician who works in the hospital. Specifically, the terminal apparatus 140 according to the first embodiment includes a stereoscopic display monitor as a display. Furthermore, the terminal apparatus 140 acquires the parallax image group from the image storage apparatus 120 and displays the acquired parallax image group on the stereoscopic display monitor. As a result, a doctor or a laboratory technician, who is an observer, may see stereoscopically viewable medical images.

Here, an explanation is given of the stereoscopic display monitor that is included in the workstation 130 and the terminal apparatus 140. Typical general-purpose monitors, which are most popular at present, display two-dimensional images in two dimensions and cannot stereoscopically display two-dimensional images. If an observer requires a stereoscopic view on the general-purpose monitor, the apparatus that outputs images to the general-purpose monitor needs to display 2 parallax images that are stereoscopically viewable by an observer in parallel by using a parallel method or an intersection method. Alternatively, the apparatus that outputs images to the general-purpose monitor needs to, for example, display an image that is stereoscopically viewable by an observer by using anaglyph that uses the glasses with the red cellophane attached to the section for the left eye and the blue cellophane attached to the section for the right eye.

Furthermore, some stereoscopic display monitors allow 2-parallax images (also referred to as binocular parallax images) to be stereoscopically viewable by using a dedicated device, such as stereoscopic-view glasses.

Figure 2A:
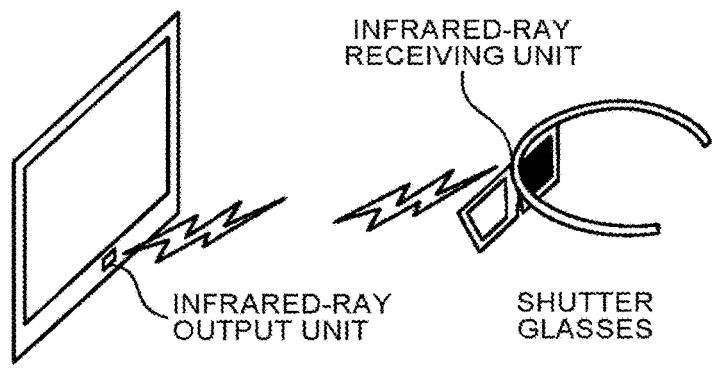
FIG. 2A is a diagram that illustrates an example of a stereoscopic display monitor that makes a stereoscopic display by using a 2-parallax image.
Figure 2B:
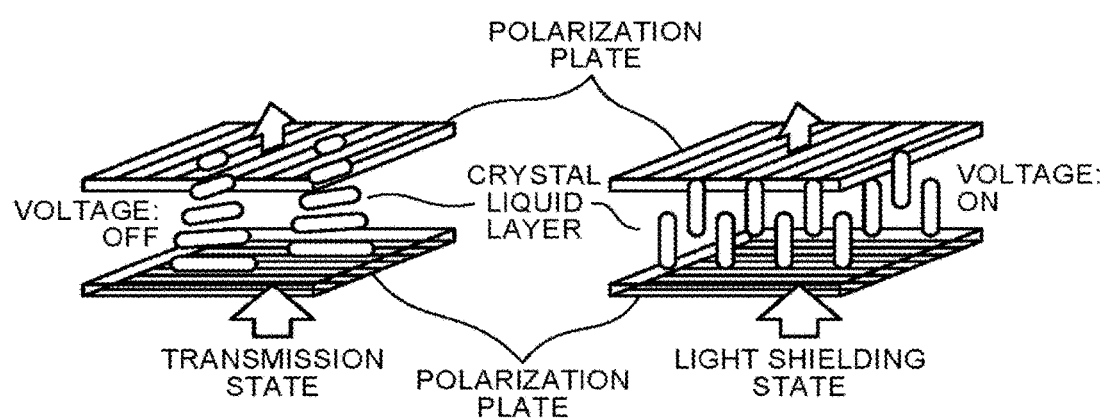
FIG. 2B is a diagram that illustrates an example of the stereoscopic display monitor that makes a stereoscopic display by using a 2-parallax image.

FIGS. 2A and 2B are diagrams that illustrate an example of the stereoscopic display monitor that makes a stereoscopic display by using a 2-parallax image. The example illustrated in FIGS. 2A and 2B is the stereoscopic display monitor that makes a stereoscopic display by using a shutter system, and shutter glasses are used as stereoscopic view glasses that are worn by the observer who observes the monitor. The stereoscopic display monitor alternately outputs 2 parallax images from the monitor. For example, the monitor illustrated in FIG. 2A alternately outputs the image for the left eye and the image for the right eye at 120 Hz. Here, as illustrated in FIG. 2A, the monitor is provided with an infrared-ray output unit, and the infrared-ray output unit controls the output of infrared rays in synchronized timing with image switching.

Furthermore, after infrared rays are output from the infrared-ray output unit, they are received by an infrared-ray receiving unit of the shutter glasses that are illustrated in FIG. 2A. A shutter is attached to the frame of each of the right and left shutter glasses, and the shutter glasses alternately switch the transmission state and the light shielding state of each of the right and left shutters in synchronized timing with the infrared-ray receiving unit receiving infrared rays. An explanation is given below of an operation to switch the transmission state and the light shielding state by the shutter.

As illustrated in FIG. 2B, each shutter includes an incidence-side polarization plate and an output-side polarization plate and further includes a crystal liquid layer between the incidence-side polarization plate and the output-side polarization plate. Furthermore, as illustrated in FIG. 2B, the incidence-side polarization plate and the output-side polarization plate are perpendicular to each other. Here, as illustrated in FIG. 2B, in the "OFF" state where the voltage is not applied, the light passes through the incidence-side polarization plate, rotates by 90 degrees due to the action of the crystal liquid layer, and then transmits through the output-side polarization plate. That is, when the voltage is not applied to the shutter, it is in the transmission state.

Conversely, as illustrated in FIG. 2B, in the state "ON" where the voltage is applied, the polarizing and rotating action by the liquid crystal molecules in the crystal liquid layer is eliminated; therefore, after the light passes through the incidence-side polarization plate, it is blocked by the output-side polarization plate. That is, when the voltage is applied to the shutter, it is in the light shielding state.

Therefore, for example, the infrared-ray output unit outputs infrared rays while the image for the left eye is displayed on the monitor. Then, while the infrared-ray receiving unit receives infrared rays, the voltage is not applied to the shutter for the left eye but the voltage is applied to the shutter for the right eye. Thus, as illustrated in FIG. 2A, the shutter for the right eye is in the light shielding state and the shutter for the left eye is in the transmission state so that the image for the left eye enters the left eye of the observer. Conversely, while the image for the right eye is displayed on the monitor, the infrared-ray output unit stops outputting infrared rays. Then, while the infrared-ray receiving unit does not receive infrared rays, the voltage is not applied to the shutter for the right eye but the voltage is applied to the shutter for the left eye. Thus, the shutter for the left eye is in the light shielding state and the shutter for the right eye is in the transmission state so that the image for the right eye enters the right eye of the observer. In this way, the stereoscopic display monitor illustrated in FIGS. 2A and 2B switches the image displayed on the monitor in conjunction with the state of the shutter, thereby displaying the image that is stereoscopically viewable by the observer. Furthermore, a monitor that uses a polarized-glasses system is known as the stereoscopic display monitor that allows a stereoscopic view of 2-parallax images, other than the above-described shutter system.

Furthermore, some of the stereoscopic display monitors, which have been recently put into practical use, allow a stereoscopic view of a multi-parallax image, such as a 9-parallax image, for an observer with the naked eye by using a light beam controller, such as a lenticular lens. The stereoscopic display monitor allows a stereoscopic view by using binocular parallax and also allows a stereoscopic view by using motion parallax with which the observed image is changed in accordance with the movement of the viewpoint of the observer.

Figure 3:
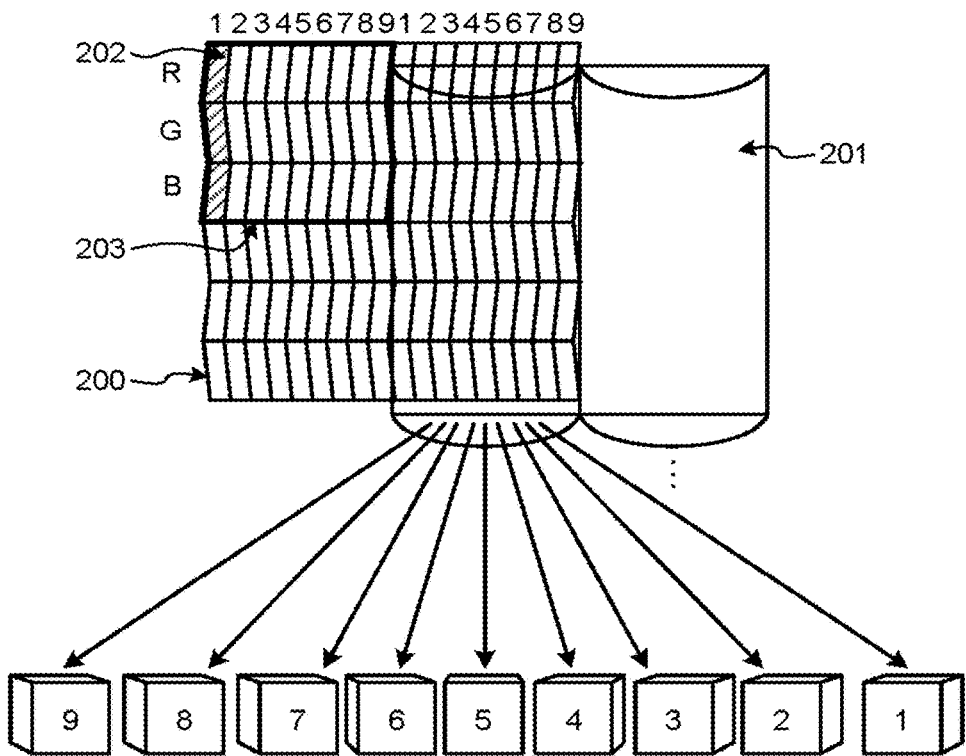
FIG. 3 is a diagram that illustrates an example of the stereoscopic display monitor that makes a stereoscopic display by using a 9-parallax image.

FIG. 3 is a diagram that illustrates an example of the stereoscopic display monitor that makes a stereoscopic display by using a 9-parallax image. The stereoscopic display monitor, illustrated in FIG. 3, is provided with a light beam controller on the front surface of a flat display plane 200, such as a liquid crystal panel. For example, in the stereoscopic display monitor that is illustrated in FIG. 3, a vertical lenticular sheet 201 with an optical aperture extending in a vertical direction is attached to the front surface of the display plane 200 as a light beam controller.

As illustrated in FIG. 3, on the display plane 200 are arranged pixels 202 in a matrix, with three sub pixels of red (R), green (G), and blue (B) arranged in a vertical direction, where the aspect ratio is 3:1. The stereoscopic display monitor, illustrated in FIG. 3, converts the 9-parallax image, which includes 9 images, into an intermediate image that is arranged with a predetermined format (e.g., a grid pattern) and then outputs it to the display plane 200. Specifically, the stereoscopic display monitor, illustrated in FIG. 3, allocates each of the 9 pixels at the same position of the 9-parallax image to the pixel 202 in 9 columns and outputs them. The pixels 202 in the 9 columns are a unit pixel group 203 for simultaneously displaying 9 images with different viewpoint positions.

The 9-parallax image, which is simultaneously output as the unit pixel group 203 on the display plane 200, is emitted as parallel light by, for example, an LED (Light Emitting Diode) backlight and further emitted in multiple directions by the vertical lenticular sheet 201. As the light of each pixel of the 9-parallax image is emitted in multiple directions, the light that enters the right eye and the left eye of the observer is changed in conjunction with the position of the observer (the position of the viewpoint). Specifically, depending on the angle of the observer's view, the parallax image that enters the right eye and the parallax image that enters the left eye have different parallactic angles. Thus, for example, the observer may stereoscopically view the capturing target at each of the 9 positions that are illustrated in FIG. 3. Furthermore, the observer may stereoscopically view the capturing target at, for example, the position of "5", illustrated in FIG. 3, while facing it and also may stereoscopically view it at each position other than "5", illustrated in FIG. 3 while the orientation of the capturing target is changed. Furthermore, the stereoscopic display monitor, illustrated in FIG. 3, is only an example. As illustrated in FIG. 3, there may be a case where the stereoscopic display monitor that displays the 9-parallax image is a horizontal-stripe liquid crystal of "RRR . . . , GGG . . . , BBB . . . ", or there may be a case where it is a vertical-stripe liquid crystal of "RGBRGB . . . ". Furthermore, as illustrated in FIG. 3, there may be a case where the stereoscopic display monitor, illustrated in FIG. 3, has a vertical-lens system where the lenticular sheet is vertical, or there may be a case where it has an oblique-lens system where the lenticular sheet is oblique.

Heretofore, a brief explanation is given of an example of the configuration of the image display system 1 according to the first embodiment. Here, the application of the above-described image display system 1 is not limited to a case where the PACS is introduced. For example, the image display system 1 is applied in a similar manner to a case where an electronic health record system is introduced to manage electronic health records with medical images attached. In this case, the image storage apparatus 120 is the database that stores electronic health records. Furthermore, for example, the image display system 1 is applied in a similar manner to a case where the HIS (Hospital Information System) or the RIS (Radiology Information System) is introduced. Furthermore, the image display system 1 is not limited to the above-described example of the configuration. The function provided by each apparatus and its assignation may be changed as appropriate depending on the operation form.

Figure 4:
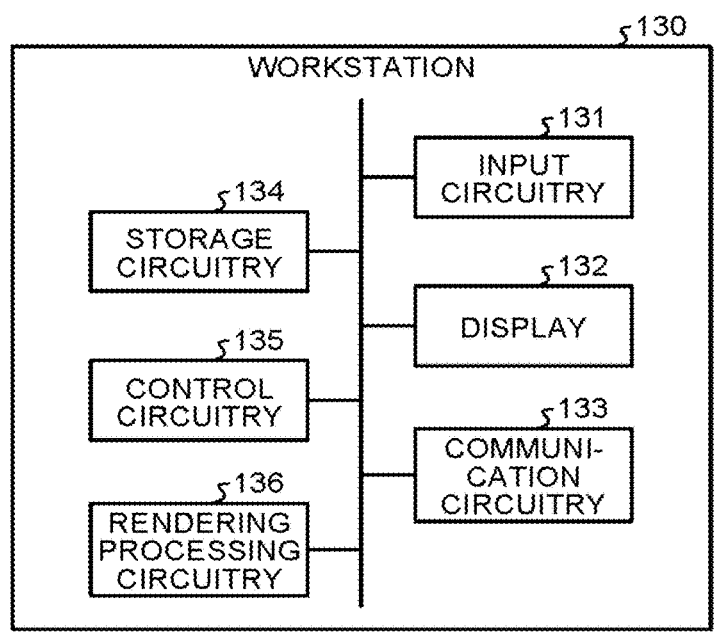
FIG. 4 is a diagram that illustrates an example of the configuration of a workstation according to the first embodiment.

Next, by using FIG. 4, an explanation is given of an example of the configuration of the workstation 130 according to the first embodiment. FIG. 4 is a diagram that illustrates an example of the configuration of the workstation according to the first embodiment. Furthermore, in the following, the "parallax image group" is the group of stereoscopic-view images that are generated by performing a volume rendering operation on volume data. Furthermore, the "parallax image" is individual image that is included in the "parallax image group". Specifically, the "parallax image group" includes multiple "parallax images" with different viewpoint positions.

The workstation 130 according to the first embodiment is a high-performance computer that is suitable for image processing, or the like and, as illustrated in FIG. 4, it includes input circuitry 131, a display 132, communication circuitry 133, storage circuitry 134, control circuitry 135, and rendering processing circuitry 136. Furthermore, an explanation is given below by using a case where the workstation 130 is a high-performance computer that is suitable for image processing, or the like; however, this is not a limitation and, it may be any information processing apparatus. For example, it may be any personal computers.

The input circuitry 131 is a mouse, keyboard, trackball, or the like, and it receives inputs of various operations to the workstation 130 from an operator. Specifically, the input circuitry 131 according to the first embodiment receives an input of the information for acquiring, from the image storage apparatus 120, the volume data that is the target for a rendering operation. For example, the input circuitry 131 receives inputs of the subject ID, the examination ID, the apparatus ID, the series ID, or the like. Furthermore, the input circuitry 131 according to the first embodiment receives an input of the condition (hereafter, a rendering condition) relating to the rendering operation.

The display 132 is a liquid crystal panel, or the like, as the stereoscopic display monitor, and it displays various types of information. Specifically, the display 132 according to the first embodiment displays a GUI (Graphical User Interface) for receiving various operations from an operator, the parallax image group, or the like. The communication circuitry 133 is a NIC (Network Interface Card), or the like, and it communicates with a different apparatus.

The storage circuitry 134 is a hard disk, a semiconductor memory device, or the like, and it stores various types of information. Specifically, the storage circuitry 134 according to the first embodiment stores the volume data that is acquired from the image storage apparatus 120 via the communication circuitry 133. Furthermore, the storage circuitry 134 according to the first embodiment stores the volume data during a rendering operation, a parallax image group that is generated due to a rendering operation, images for two-dimensional display, or the like.

The control circuitry 135 is an electronic circuit, such as a CPU (Central Processing Unit) or a MPU (Micro Processing Unit), or an integrated circuit, such as an ASIC (Application Specific Integrated Circuit) or FPGA (Field Programmable Gate Array), and it performs the overall control on the workstation 130.

For example, the control circuitry 135 according to the first embodiment controls the display of a GUI and the display of a parallax image group on the display 132. Furthermore, for example, the control circuitry 135 controls transmission and reception of volume data or a parallax image group, performed with the image storage apparatus 120 via the communication circuitry 133. Furthermore, for example, the control circuitry 135 controls a rendering operation by the rendering processing circuitry 136. Moreover, for example, the control circuitry 135 controls reading of volume data from the storage circuitry 134 and storing of a parallax image group in the storage circuitry 134.

Under the control of the control circuitry 135, the rendering processing circuitry 136 performs various rendering operations on volume data that is acquired from the image storage apparatus 120, thereby generating a parallax image group. Specifically, the rendering processing circuitry 136 according to the first embodiment reads volume data from the storage circuitry 134 and first performs preprocessing on the volume data. Next, the rendering processing circuitry 136 performs a volume rendering operation on the preprocessed volume data, thereby generating a parallax image group. Next, the rendering processing circuitry 136 generates a two-dimensional image, in which various types of information (scale, subject name, examination item, or the like) is rendered, and overlays it on each parallax image group, thereby generating a two-dimensional image for output. Then, the rendering processing circuitry 136 stores the generated parallax image group and the two-dimensional image for output in the storage circuitry 134. Here, according to the first embodiment, the rendering operation is the entire image processing that is performed on volume data, and the volume rendering operation is, among the rendering operation, the operation to generate a two-dimensional image in which three-dimensional information is applied. Medical images that are generated during the rendering operation correspond to, for example, parallax images.

Figure 5:
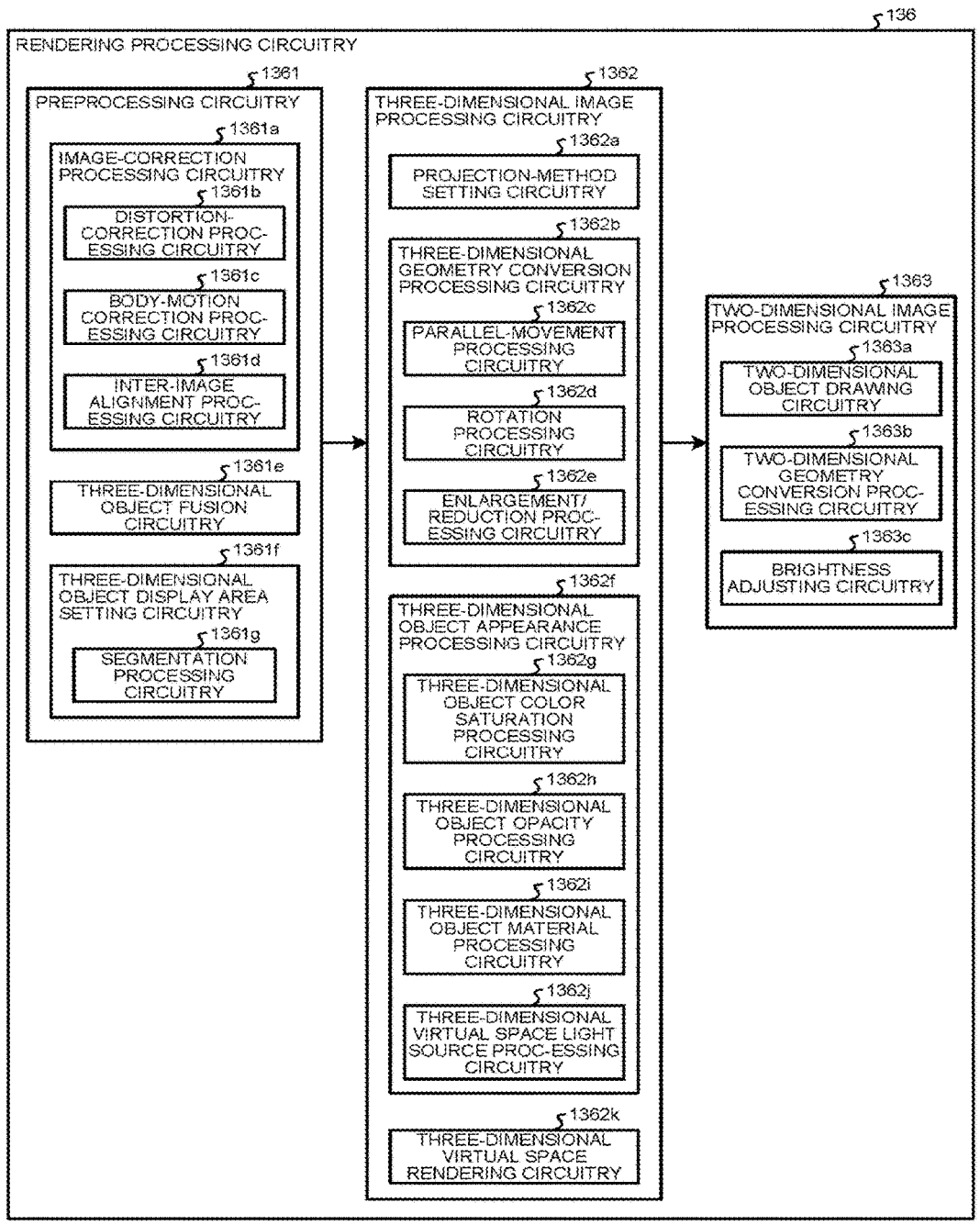
FIG. 5 is a diagram that illustrates an example of the configuration of rendering processing circuitry that is illustrated in FIG. 4.

FIG. 5 is a diagram that illustrates an example of the configuration of the rendering processing circuitry that is illustrated in FIG. 4. As illustrated in FIG. 5, the rendering processing circuitry 136 includes preprocessing circuitry 1361, three-dimensional image processing circuitry 1362, and two-dimensional image processing circuitry 1363. The preprocessing circuitry 1361 performs preprocessing on volume data, the three-dimensional image processing circuitry 1362 generates a parallax image group from the preprocessed volume data, and the two-dimensional image processing circuitry 1363 generates a two-dimensional image for output with various types of information overlaid on the parallax image group. Each circuitry is sequentially explained below.

The preprocessing circuitry 1361 is processing circuitry that performs various types of preprocessing when a rendering operation is performed on volume data, and it includes image-correction processing circuitry 1361a, three-dimensional object fusion circuitry 1361e, and three-dimensional object display area setting circuitry 1361f.

The image-correction processing circuitry 1361a is processing circuitry that performs an image correction operation when two types of volume data is processed as single volume data and, as illustrated in FIG. 5, it includes distortion-correction processing circuitry 1361b, body-motion correction processing circuitry 1361c, and inter-image alignment processing circuitry 1361d. For example, the image-correction processing circuitry 1361a performs an image correction operation when the volume data on a PET image and the volume data on an X-ray CT image, generated by a PET-CT apparatus, are processed as single volume data. Alternatively, the image-correction processing circuitry 1361a performs an image correction operation when the volume data on a T1 weighted image and the volume data on a T2 weighted image, generated by an MRI apparatus, are processed as single volume data.

Furthermore, with regard to individual volume data, the distortion-correction processing circuitry 1361b corrects distortion of the data due to the acquisition condition during acquisition of the data by the medical-image diagnostic apparatus 110. Furthermore, the body-motion correction processing circuitry 1361c corrects the movement due to the body motion of the subject at the time when data is acquired to be used for generating individual volume data. Furthermore, the inter-image alignment processing circuitry 1361d conducts alignment (Registration) by using, for example, the cross-correlation method on two sets of volume data on which the correction operations have been performed by the distortion-correction processing circuitry 1361b and the body-motion correction processing circuitry 1361c.

The three-dimensional object fusion circuitry 1361e fuses multiple sets of volume data on which alignment has been conducted by the inter-image alignment processing circuitry 1361d. Here, the operations of the image-correction processing circuitry 1361a and the three-dimensional object fusion circuitry 1361e are omitted if a rendering operation is performed on single volume data.

The three-dimensional object display area setting circuitry 1361f is processing circuitry that sets the display area that corresponds to the display target organ that is designated by the operator, and it includes segmentation processing circuitry 1361g. The segmentation processing circuitry 1361g is processing circuitry that extracts organs, such as the heart, lung, or blood vessel, designated by the operator, by using a region growing method based on the pixel values (voxel values) of volume data, for example.

Furthermore, the segmentation processing circuitry 1361*g* does not perform a segmentation operation if the operator does not designate the display target organ. Furthermore, if the operator designates multiple display target organs, the segmentation processing circuitry 1361*g* extracts the corresponding organs. Moreover, the operation of the segmentation processing circuitry 1361*g* is sometimes performed again in accordance with a request for fine adjustment from the operator who sees the rendering image.

The three-dimensional image processing circuitry 1362 performs a volume rendering operation on the preprocessed volume data that has been processed by the preprocessing circuitry 1361. As a processing circuitry that performs a volume rendering operation, the three-dimensional image processing circuitry 1362 includes projection-method setting circuitry 1362*a*, three-dimensional geometry conversion processing circuitry 1362*b*, three-dimensional object appearance processing circuitry 1362*f*, and three-dimensional virtual space rendering circuitry 1362*k*.

The projection-method setting circuitry 1362*a* determines a projection method for generating a parallax image group. For example, the projection-method setting circuitry 1362*a* determines whether a volume rendering operation is performed with a parallel projection method or is performed with a perspective projection method.

The three-dimensional geometry conversion processing circuitry 1362*b* is processing circuitry that determines the information for converting the volume data, on which a volume rendering operation is performed, in a three-dimensional geometric manner, and it includes parallel-movement processing circuitry 1362*c*, rotation processing circuitry 1362*d*, and enlargement/reduction processing circuitry 1362*e*. The parallel-movement processing circuitry 1362*c* is processing circuitry that determines the amount of movement with which volume data is moved in parallel when the viewpoint position is moved in parallel during execution of a volume rendering operation, and the rotation processing circuitry 1362*d* is processing circuitry that determines the amount of movement with which volume data is rotated and moved when the viewpoint position is rotated and moved during execution of a volume rendering operation. Furthermore, the enlargement/reduction processing circuitry 1362*e* is processing circuitry that determines the enlargement rate or the reduction rate of volume data when a request is made to enlarge or reduce a parallax image group.

The three-dimensional object appearance processing circuitry 1362*f* includes three-dimensional object color saturation processing circuitry 1362*g*, three-dimensional object opacity processing circuitry 1362*h*, three-dimensional object material processing circuitry 1362*i*, and three-dimensional virtual space light source processing circuitry 1362*j*. With these processing circuitry, for example, the three-dimensional object appearance processing circuitry 1362*f* performs an operation to determine the display status of the displayed parallax image group in response to a request from an operator.

The three-dimensional object color saturation processing circuitry 1362*g* is processing circuitry that determines the color that is painted on each area of volume data, on which segmentation has been conducted. The three-dimensional object opacity processing circuitry 1362*h* is processing circuitry that determines the opacity (Opacity) of each voxel included in each area of the volume data, on which segmentation has been conducted. Here, the area, in the volume data, that is behind the area, for which it is determined that the opacity is "100%", is not rendered in the parallax image group. Furthermore, the area, in volume data, for which it is determined that the opacity is "0%" is not rendered in the parallax image group.

The three-dimensional object material processing circuitry 1362*i* is processing circuitry that determines the material of each area of the volume data, on which segmentation has been conducted, thereby adjusting the texture upon rendering of the area. The three-dimensional virtual space light source processing circuitry 1362*j* is processing circuitry that determines the position of the virtual light source, which is provided in a three-dimensional virtual space, and the type of the virtual light source when a volume rendering operation is performed on the volume data. The type of virtual light source includes a light source that emits parallel light beams from the infinity, a light source that emits radial light beams from the viewpoint, or the like.

The three-dimensional virtual space rendering circuitry 1362*k* performs a volume rendering operation on volume data, thereby generating a parallax image group. Furthermore, when the three-dimensional virtual space rendering circuitry 1362*k* performs a volume rendering operation, it uses various types of information that is determined by the projection-method setting circuitry 1362*a*, the three-dimensional geometry conversion processing circuitry 1362*b*, and the three-dimensional object appearance processing circuitry 1362*f* as needed.

Here, the three-dimensional virtual space rendering circuitry 1362*k* performs a volume rendering operation in accordance with a rendering condition. For example, the rendering condition is "parallel projection method" or "perspective projection method". Furthermore, the rendering condition is, for example, "reference viewpoint position and parallactic angle". Furthermore, the rendering condition is, for example, "parallel movement of the viewpoint position", "rotational movement of the viewpoint position", "enlargement of a parallax image group", or "reduction of a parallax image group". Furthermore, the rendering condition is, for example, "color to be painted", "transparency", "texture", "position of the virtual light source", or "type of the virtual light source". It is possible that there is a case where the above rendering condition is received from an operator via the input circuitry 131 or a case where it is set by default. In any case, the three-dimensional virtual space rendering circuitry 1362*k* receives a rendering condition from the control circuitry 135 and performs a volume rendering operation on volume data in accordance with the rendering condition. Furthermore, at this point, as the projection-method setting circuitry 1362*a*, the three-dimensional geometry conversion processing circuitry 1362*b*, and the three-dimensional object appearance processing circuitry 1362*f*, described above, determine various types of necessary information in accordance with the rendering condition, the three-dimensional virtual space rendering circuitry 1362*k* uses the various types of determined information to generate a parallax image group.

Figure 6:
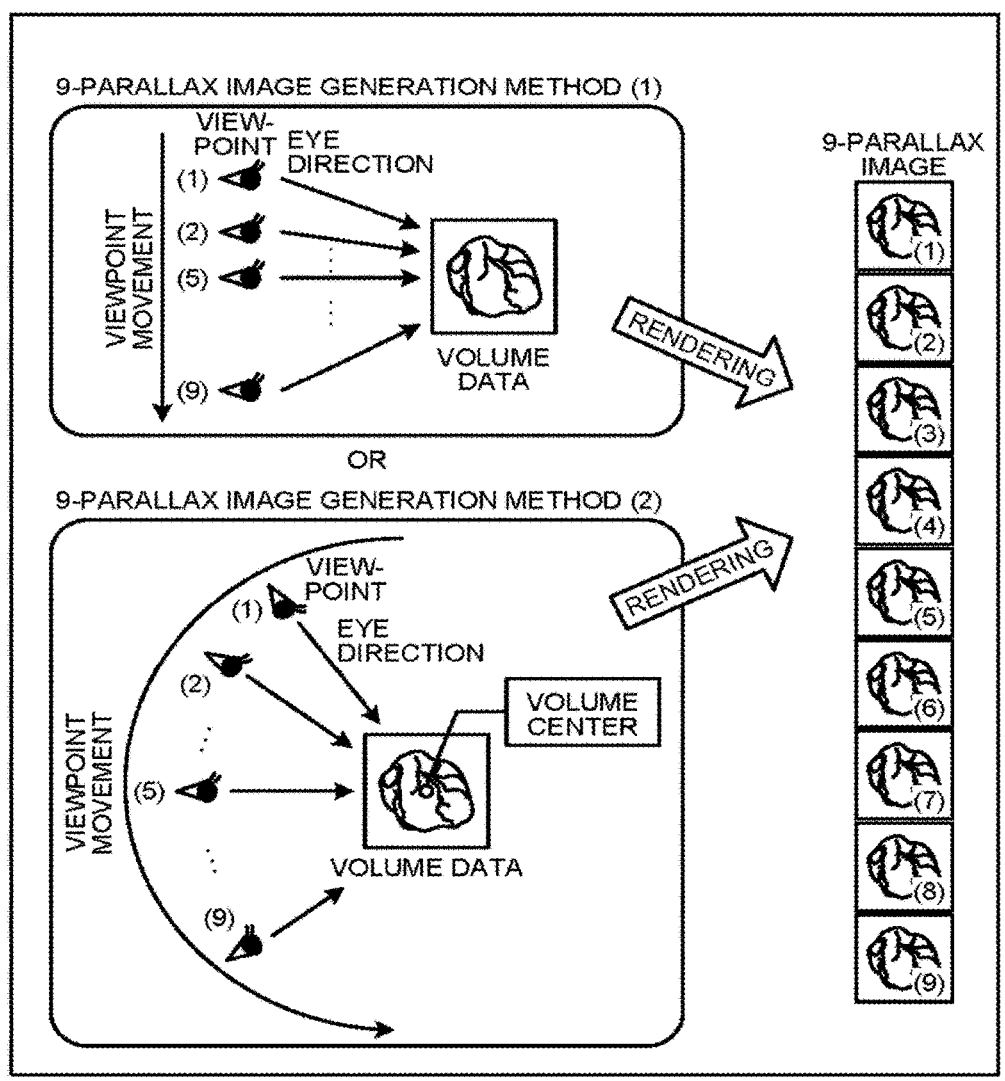
FIG. 6 is a diagram that illustrates an example of the volume rendering operation according to the first embodiment.

FIG. 6 is a diagram that illustrates an example of the volume rendering operation according to the first embodiment. For example, as illustrated in the "9-parallax image generation method (1)" of FIG. 6, the three-dimensional virtual space rendering circuitry 1362*k* receives a parallel projection method as the rendering condition and further receives the reference viewpoint position (5) and the parallactic angle of "1 degree". In such a case, the three-dimensional virtual space rendering circuitry 1362*k* moves the position of the viewpoint from (1) to (9) in parallel at intervals of the parallactic angle of "1 degree", thereby generating 9 parallax images with a different parallactic angle (the angle between the lines of sight) by 1 degree according to a parallel projection method. Furthermore, if the parallel projection method is implemented, the three-dimensional virtual space rendering circuitry 1362k sets the light source that emits parallel light beams from the infinity along the eye direction.

Alternatively, as illustrated in "9-parallax image generation method (2)" of FIG. 6, the three-dimensional virtual space rendering circuitry 1362k receives a perspective projection method as the rendering condition and further receives the reference viewpoint position (5) and the parallactic angle of "1 degree". In such a case, the three-dimensional virtual space rendering circuitry 1362k rotates and moves the position of the viewpoint from (1) to (9) around the center (the center of gravity) of the volume data at the intervals of the parallactic angle of "1 degree", thereby generating 9 parallax images with different parallactic angles by 1 degree according to the perspective projection method. Furthermore, if the perspective projection method is implemented, the three-dimensional virtual space rendering circuitry 1362k sets a point light source or a surface light source that radially emits light in three dimensions in the eye direction at the center with regard to each viewpoint. Moreover, if the perspective projection method is implemented, there may be a case where the viewpoints (1) to (9) are moved in parallel depending on the rendering condition.

Furthermore, the three-dimensional virtual space rendering circuitry 1362k may perform a volume rendering operation using a parallel projection method and a perspective projection method in combination by setting the light source that radially emits light in two dimensions in the eye direction as the center with respect to the vertical direction of the displayed volume rendering image and that emits parallel light beams from the infinity along the eye direction with respect to the horizontal direction of the displayed volume rendering image.

The 9 parallax images, generated as above, are a parallax image group. According to the first embodiment, the 9 parallax images are converted into an intermediate image that is arranged with a predetermined format (e.g., a grid pattern) by, for example, the control circuitry 135 and is output to the display 132 as the stereoscopic display monitor. Then, an operator of the workstation 130 may perform an operation to generate a parallax image group while it checks a stereoscopically viewable medical image that is displayed on the stereoscopic display monitor.

Furthermore, in the example of FIG. 6, an explanation is given of a case where the projection method, the reference viewpoint position, and the parallactic angle are received as the rendering conditions; however, in a case where different conditions are received as the rendering conditions, the three-dimensional virtual space rendering circuitry 1362k generates a parallax image group in the same manner, while each of the rendering conditions is applied.

Furthermore, in addition to the volume rendering, the three-dimensional virtual space rendering circuitry 1362k reconstructs a planar image with an arbitrary planar surface (e.g., an axial plane, sagittal plane, or coronal plane). For example, the three-dimensional virtual space rendering circuitry 1362k implements a cross-sectional reconstruction method (MPR: Multi Planer Reconstruction) to reconstruct an MPR image from volume data. Furthermore, the three-dimensional virtual space rendering circuitry 1362k has a function to conduct "Curved MPR" or a function to conduct "Intensity Projection".

Furthermore, the parallax image group that is generated from volume data by the three-dimensional image processing circuitry 1362 is an underlay (Underlay). Moreover, the underlay is superimposed with an overlay (Overlay) in which various types of information (scale, subject name, examination item, or the like) is rendered, whereby a two-dimensional image for output is obtained. The two-dimensional image processing circuitry 1363 is processing circuitry that performs image processing on the overlay and the underlay, thereby generating a two-dimensional image for output and, as illustrated in FIG. 5, it includes two-dimensional object drawing circuitry 1363a, two-dimensional geometry conversion processing circuitry 1363b, and brightness adjusting circuitry 1363c. For example, to reduce the loads required for an operation to generate a two-dimensional image for output, the two-dimensional image processing circuitry 1363 superimposes a single overlay on each of the 9 parallax images (underlays), thereby generating 9 two-dimensional images for output.

The two-dimensional object drawing circuitry 1363a is processing circuitry that draws various types of information that is rendered to the overlay, and the two-dimensional geometry conversion processing circuitry 1363b is processing circuitry that performs an operation for a parallel movement or an operation for a rotational movement of the positions of various types of information that is rendered to the overlay or that performs an operation for enlargement or an operation for reduction of various types of information that is rendered to the overlay.

Furthermore, the brightness adjusting circuitry 1363c is processing circuitry that performs an operation to change the brightness, and it is processing circuitry that adjusts the brightness of overlay and underlay in accordance with, for example, the tone of the stereoscopic display monitor, which is the output destination, or image processing parameters, such as the window width (WW: Window Width) or window level (WL: Window Level).

The two-dimensional image for output, generated as above, is temporarily stored in the storage circuitry 134 by the control circuitry 135, for example, and then transmitted to the image storage apparatus 120 via the communication circuitry 133. For example, if the terminal apparatus 140 acquires the two-dimensional image for output from the image storage apparatus 120, converts it into an intermediate image that is arranged with a predetermined format (e.g., a grid pattern), and then displays it on the stereoscopic display monitor, a doctor or a laboratory technician, who is an observer, may see a stereoscopically viewable medical image in a state such that various types of information (scale, subject name, examination item, or the like) is rendered.

The configurations of the image display system 1 and the workstation 130 according to the first embodiment are explained above. With these configurations, the workstation 130 according to the first embodiment is configured to allow a display of an easily observable medical image in a stable manner due to the operation of the control circuitry 135, described below in detail. Here, an explanation is first given of a case where it is difficult to display an easily observable medical image in a stable manner according to a conventional technology. Furthermore, in the following, a stereoscopically viewable three-dimensional image is sometimes referred to as a stereoscopic image.

Conventionally, volume data that is acquired by various medical-image diagnostic apparatus has a different resolution size, such as pixel, the slice thickness, the number of pixels, or the enlargement rate; therefore, if a stereoscopic image is generated by using the acquired volume data without change, the display size of each medical image varies, or the appearance of solidity differs (e.g., excess and deficiency of the degree of protrusion).

Figure 7:
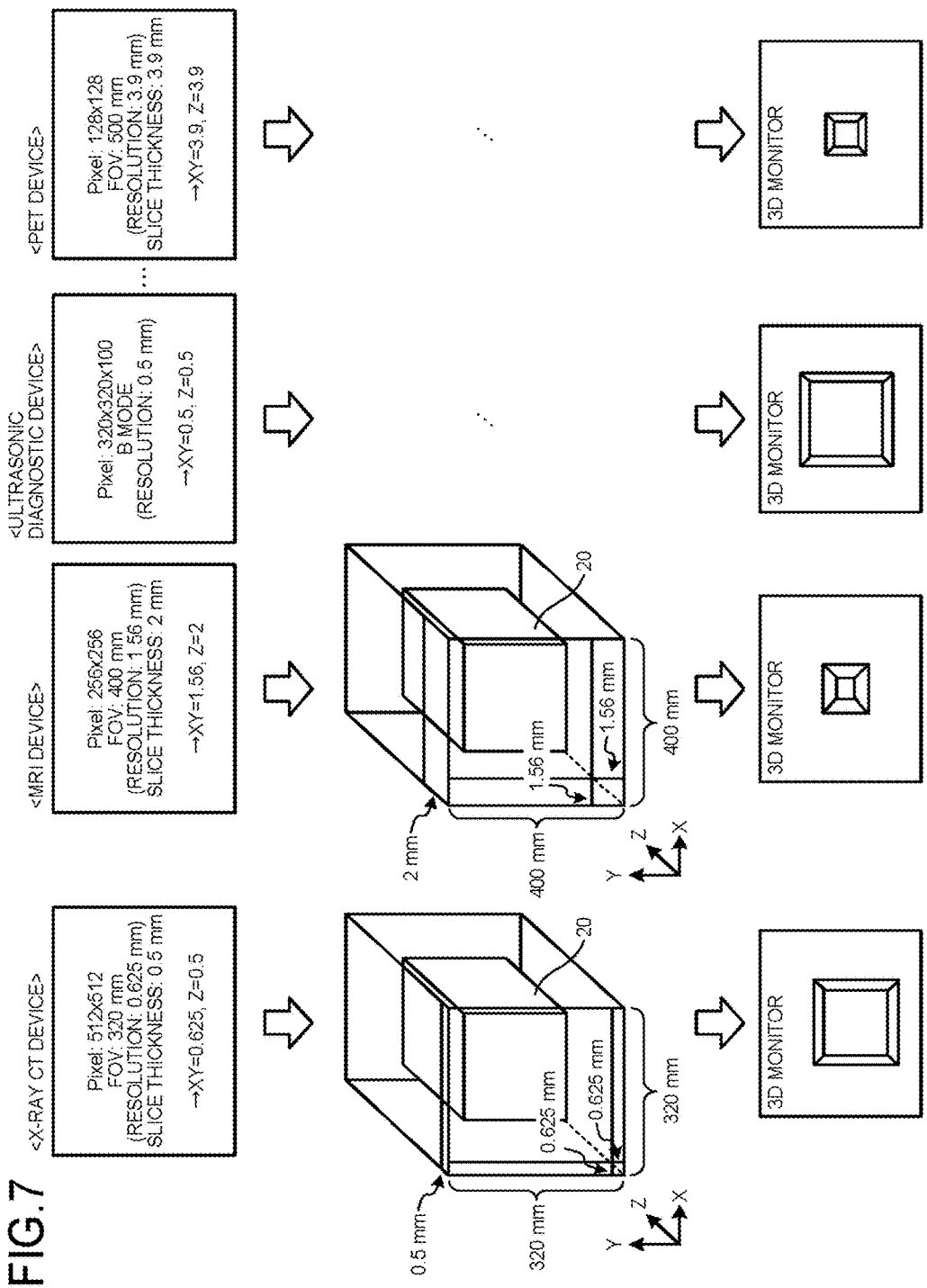
FIG. 7 is a diagram that illustrates an example of the problem relating to the conventional technology.

FIG. 7 is a diagram that illustrates an example of the problem relating to the conventional technology. FIG. 7 illustrates an example of a case where a stereoscopic image is generated by using volume data without change, acquired by an X-ray CT apparatus, an MRI apparatus, an ultrasonic diagnostic apparatus, and a PET apparatus as medical-image diagnostic apparatus, and it is displayed on a 3D monitor that is a stereoscopically viewable monitor. For example, as illustrated in FIG. 7, as for volume data that is acquired by the X-ray CT apparatus, volume data is constructed as "Pixel: 512×512", "FOV (Field of View): 320 mm", and "slice thickness: 0.5 mm". Specifically, as illustrated in FIG. 7, the resolution (resolution performance) of the volume data including a site of interest 20 is "0.625 (=320/512) mm" (indicated as XY=0.625 in the drawing) in the axis-X and axis-Y direction and "0.5 mm" (indicated as Z=0.5 in the drawing) in the axis-Z direction.

Conversely, as for volume data that is acquired by the MRI apparatus, for example, volume data is constructed as "Pixel: 256×256", "FOV: 400 mm", and "slice thickness: 2 mm". Specifically, as illustrated in FIG. 7, the resolution (resolution performance) of the volume data including the site of interest 20 is "1.56 (=400/256) mm" (indicated as XY=1.56 in the drawing) in the axis-X and axis-Y direction and "2 mm" (indicated as Z=2 in the drawing) in the axis-Z direction.

Therefore, if a stereoscopic image (a parallax image group) is generated by using the above volume data without change and is displayed on the same 3D monitor, the CT image is larger in size and furthermore the degree of protrusion is smaller compared to the MR image, as illustrated in FIG. 7, due to the different voxel size. Similarly, as for volume data that is acquired by the ultrasonic diagnostic apparatus, for example, as illustrated in FIG. 7, it is constructed as "Pixel: 320×320×100" and "B mode (resolution: 0.5 mm)", and "XY=0.5, Z=0.5" is obtained. Furthermore, as for volume data that is acquired by the PET apparatus, for example, as illustrated in FIG. 7, volume data is constructed as "Pixel: 128×128", "FOV: 500 mm", "(resolution: 3.9 mm)" and "slice thickness: 3.9 mm", and "XY=3.9, Z=3.9" is obtained. As for them, if a stereoscopic image is generated by using the above volume data without change and is displayed on the 3D monitor, the size is different and the degree of protrusion is different compared to other stereoscopic images, as illustrated in FIG. 7.

Thus, according to the conventional technology, if a stereoscopic image is generated and displayed by using volume data that is acquired by each medical-image diagnostic apparatus without change, it is difficult to display an easily observable medical image in a stable manner. Therefore, the workstation 130 according to the first embodiment reconstructs volume data on the basis of the resolution of each volume data and then generates and displays a stereoscopic image; thus, easily observable medical images may be displayed in a stable manner.

Figure 8:
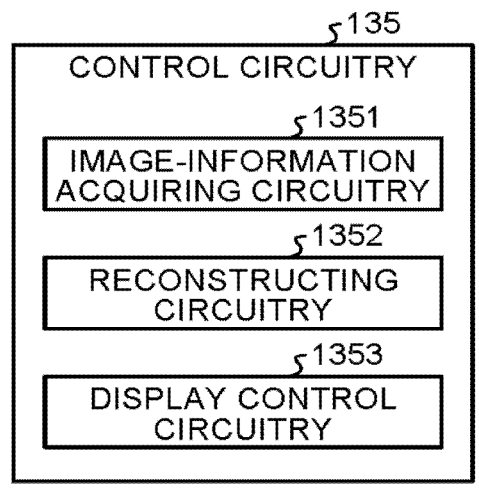
FIG. 8 is a diagram that illustrates an example of the configuration of control circuitry according to the first embodiment.

FIG. 8 is a diagram that illustrates an example of the configuration of the control circuitry 135 according to the first embodiment. As illustrated in FIG. 8, the control circuitry 135 includes image-information acquiring circuitry 1351, reconstructing circuitry 1352, and display control circuitry 1353. The image-information acquiring circuitry 1351 acquires the image information of the medical image data for displaying a stereoscopic image on the stereoscopically viewable display. Specifically, when the image-information acquiring circuitry 1351 acquires volume data for generating and displaying a stereoscopic image from the medical-image diagnostic apparatus 110 or the image storage apparatus 120, it acquires the information relating to the FOV or the resolution (resolution performance) of the volume data. For example, the image-information acquiring circuitry 1351 acquires the size of the resolution, such as pixel, the slice thickness, the number of pixels, or the enlargement rate, with regard to volume data that is stored in the storage circuitry 134. The image-information acquiring circuitry 1351, for example, acquires the pixel, the slice thickness, the number of pixels, or the like, from the tag of DICOM. Furthermore, the image-information acquiring circuitry 1351 acquires information on the enlargement rate that is designated by the operator. Furthermore, the image-information acquiring circuitry 1351 may acquire, from the tag of DICOM, the information, such as the magnification, in a case where an enlargement reconstruction is performed (for example, in a case where the FOV during the reconstruction is 200 although the FOV during the capturing is 400).

The reconstructing circuitry 1352 reconstructs the resolution of the medical image data into a predetermined resolution on the basis of the image information on the medical image data that is acquired by the image-information acquiring circuitry 1351. Specifically, the reconstructing circuitry 1352 reconstructs the resolution of the volume data by using, as the predetermined resolution, the highest value among the resolutions that are included in the image information on the volume data that is acquired by the image-information acquiring circuitry 1351.

For example, the reconstructing circuitry 1352 extracts the value with the highest resolution with regard to the resolution, the slice thickness, or the reconstruction interval of each volume data that is acquired by each of the medical-image diagnostic apparatus 110, such as the X-ray CT apparatus, or the MRI apparatus. Then, the reconstructing circuitry 1352 reconstructs each volume data, acquired by each of the medical-image diagnostic apparatus 110, with the extracted resolution.

Then, the reconstructing circuitry 1352 controls the rendering processing circuitry 136 so as to perform a volume rendering operation by moving the viewpoint position by a predetermined parallactic angle relative to the volume data and generate a parallax image group that includes a plurality of parallax images with different viewpoint positions. Here, the reconstructing circuitry 1352 controls the rendering processing circuitry 136 so as to adjust each parallactic angle during generation of the parallax image group with regard to the volume data that is acquired by each of multiple types of medical-image diagnostic apparatus and, in accordance with each of the adjusted parallactic angles, generate each parallax image group on the basis of the volume data that is acquired by each of the multiple types of medical-image diagnostic apparatus. That is, the reconstructing circuitry 1352 controls the rendering processing circuitry 136 so as to adjust, with respect to each volume data, the parallactic angle during generation of the parallax image group from each volume data. Furthermore, the reconstructing circuitry 1352 is also referred to as generating circuitry.

The display control circuitry 1353 displays, on the display circuitry 132, the stereoscopic image that is generated by using the medical image data that is reconstructed into a predetermined resolution by the reconstructing circuitry 1352. Specifically, the display control circuitry 1353 uses the volume data that is reconstructed by the reconstructing circuitry 1352 to display, on the display 132, the parallax image group that is generated by the rendering processing circuitry 136.

Figure 9:
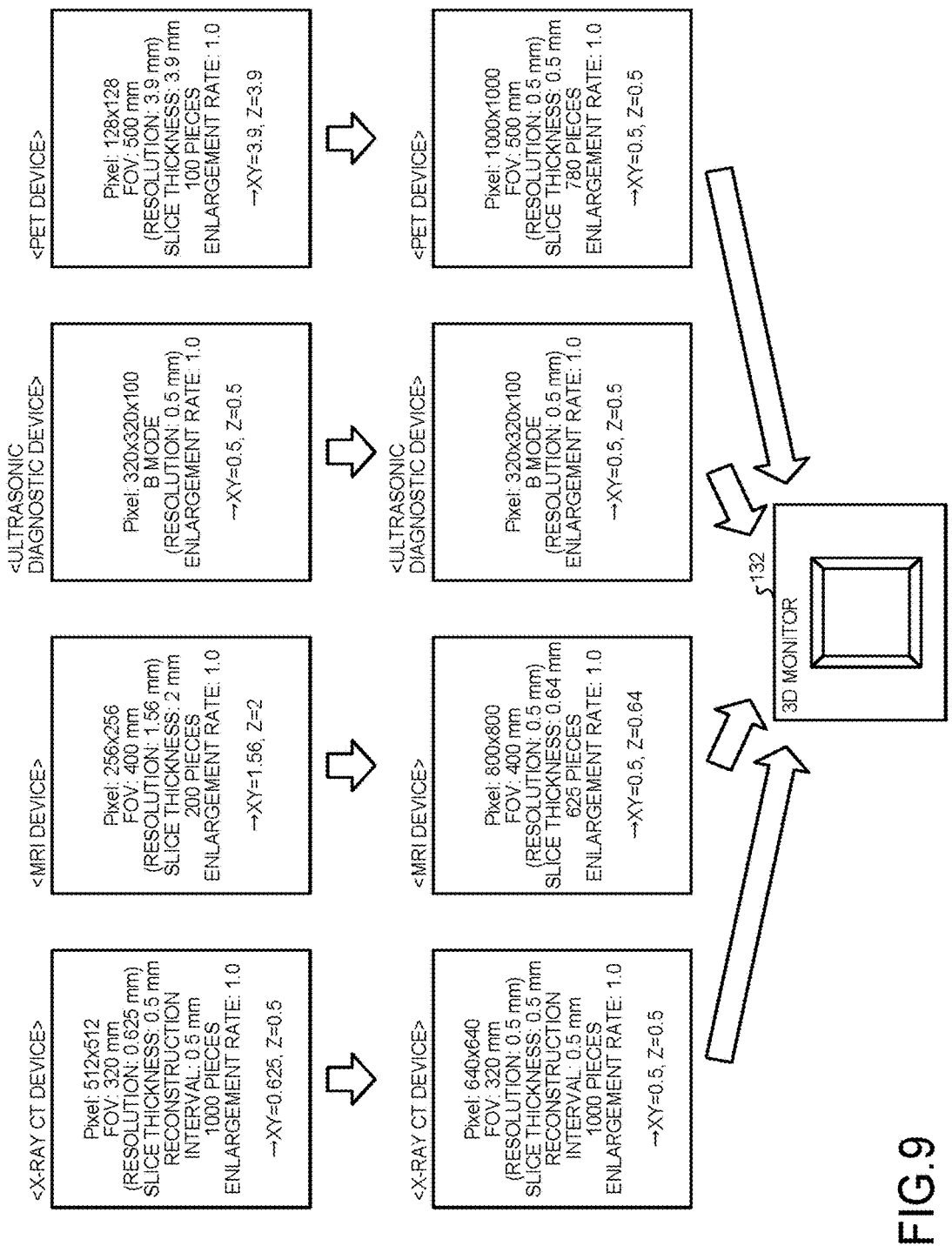
FIG. 9 is a diagram that illustrates an example of the operation by the workstation according to the first embodiment.

FIG. 9 is a diagram that illustrates an example of the operation by the workstation 130 according to the first embodiment. FIG. 9 illustrates an operation in a case where the CT image acquired by the X-ray CT apparatus, the MR image acquired by the MRI apparatus, the ultrasonic image acquired by the ultrasonic diagnostic apparatus, and the PET image acquired by the PET apparatus are displayed as stereoscopic images with regard to the same site of interest. Here, the example illustrated in FIG. 9 is only an example, and this is not a limitation on the embodiment.

For example, in the workstation 130 according to the first embodiment, as illustrated in FIG. 9, the image-information acquiring circuitry 1351 acquires the image information on the volume data for each of the CT image, the MR image, the ultrasonic image, and the PET image. For example, the image-information acquiring circuitry 1351 acquires, as the image information on the CT image, "Pixel: 512×512", "FOV: 320 mm", "resolution: 0.625 mm", "slice thickness: 0.5 mm", "reconstruction interval: 0.5 mm", "1000 pieces", and "enlargement rate: 1.0". Specifically, the image-information acquiring circuitry 1351 acquires "XY=0.625 mm" and "Z=0.5 mm" as the information on the resolution of the CT image, as illustrated in FIG. 9. Furthermore, the value designated by the operator is acquired as the above-described enlargement rate.

Furthermore, the image-information acquiring circuitry 1351 acquires, as the image information on the MR image, "Pixel: 256×256", "FOV: 400 mm", "resolution: 1.56 mm", "slice thickness: 2 mm", "200 pieces", and "enlargement rate: 1.0". That is, the image-information acquiring circuitry 1351 acquires "XY=1.56 mm" and "Z=2 mm" as the information on the resolution of the MR image, as illustrated in FIG. 9. Furthermore, the value that is designated by the operator is acquired as the above-described enlargement rate.

Furthermore, the image-information acquiring circuitry 1351 acquires, as the image information on the ultrasonic image, "Pixel: 320×320×100", "B mode resolution: 0.5 mm", and "enlargement rate: 1.0". That is, the image-information acquiring circuitry 1351 acquires "XY=0.5 mm" and "Z=0.5 mm" as the information on the resolution of the ultrasonic image, as illustrated in FIG. 9. Furthermore, the value that is designated by the operator is acquired as the above-described enlargement rate.

Furthermore, the image-information acquiring circuitry 1351 acquires, as the image information on the PET image, "Pixel: 128×128", "FOV: 500 mm", "resolution: 3.9 mm", "slice thickness: 3.9 mm", "100 pieces", and "enlargement rate: 1.0". That is, the image-information acquiring circuitry 1351 acquires "XY=3.9 mm" and "Z=3.9 mm" as the information on the resolution of the ultrasonic image, as illustrated in FIG. 9. Furthermore, the value that is designated by the operator is acquired as the above-described enlargement rate.

Then, the reconstructing circuitry 1352 reconstructs the volume data on each medical image into a predetermined resolution in the image information on the volume data that is acquired by the image-information acquiring circuitry 1351. Here, the reconstructing circuitry 1352 reconstructs it into, for example, the resolution with the highest value among the resolutions that are included in the image information on the volume data that is acquired by the image-information acquiring circuitry 1351.

For example, the reconstructing circuitry 1352 extracts the value with the highest resolution (the value with the smallest number) from the image information on the volume data on each medical image that is illustrated in FIG. 9. That is, the reconstructing circuitry 1352 extracts, from the value "XY" and the value "Z" in each volume data, "0.5 mm" that is the resolution in the direction "Z" of the CT image or the direction "XY", "Z" of the ultrasonic image.

Then, the reconstructing circuitry 1352 reconstructs each volume data into the extracted resolution. For example, the reconstructing circuitry 1352 reconstructs the resolution of each volume data into the extracted "0.5 mm", as illustrated in FIG. 9. Specifically, the reconstructing circuitry 1352 reconstructs, for example, the volume data on the CT image as "Pixel: 640×640 (=320/0.5)", "FOV: 320 mm", "resolution: 0.5 mm", "slice thickness: 0.5 mm", "reconstruction interval: 0.5 mm", "1000 pieces", and "enlargement rate: 1.0". That is, the reconstructing circuitry 1352 sets the volume data on the CT image to "XY=0.5 mm" and "Z=0.5 mm", as illustrated in FIG. 9.

Furthermore, the reconstructing circuitry 1352 reconstructs, for example, the volume data on the MR image as "Pixel: 800×800 (=400/0.5)", "FOV: 400 mm", "resolution: 0.5 mm", "slice thickness: 0.64 mm (=2/800/256)", "625 pieces (=2×200/0.64)", and "enlargement rate: 1.0". That is, the reconstructing circuitry 1352 sets the volume data on the MR image to "XY=0.5 mm" and "Z=0.64 mm", as illustrated in FIG. 9.

Furthermore, as the volume data on the ultrasonic image is "XY=0.5 mm" and "Z=0.5 mm", for example, the reconstructing circuitry 1352 does not perform reconstruction but sets the data without change.

Furthermore, the reconstructing circuitry 1352 reconstructs, for example, the volume data on the PET image to "Pixel: 1000×1000 (=500/0.5)", "FOV: 500 mm", "resolution: 0.5 mm", "slice thickness: 0.5 mm (=3.9/100/128)", "780 pieces (=1×390/0.5)", and "enlargement rate: 1.0". That is, the reconstructing circuitry 1352 sets the volume data on the PET image to "XY=0.5 mm" and "Z=0.5 mm", as illustrated in FIG. 9.

As described above, the reconstructing circuitry 1352 reconstructs the volume data on each medical image. Then, the reconstructing circuitry 1352 controls the rendering processing circuitry 136 so as to perform a volume rendering operation with the adjusted parallactic angle during generation of a parallax image group with regard to each reconstructed volume data. For example, the reconstructing circuitry 1352 adjusts each parallactic angle during generation of a parallax image group with regard to volume data that is acquired by each of the multiple types of medical-image diagnostic apparatus such that the degree of protrusion is matched during display on the display 132 as the stereoscopic display monitor, and it generates each parallax image group on the basis of the volume data that is acquired by each of the multiple types of the medical-image diagnostic apparatus in accordance with each of the adjusted parallactic angles.

Figure 10:
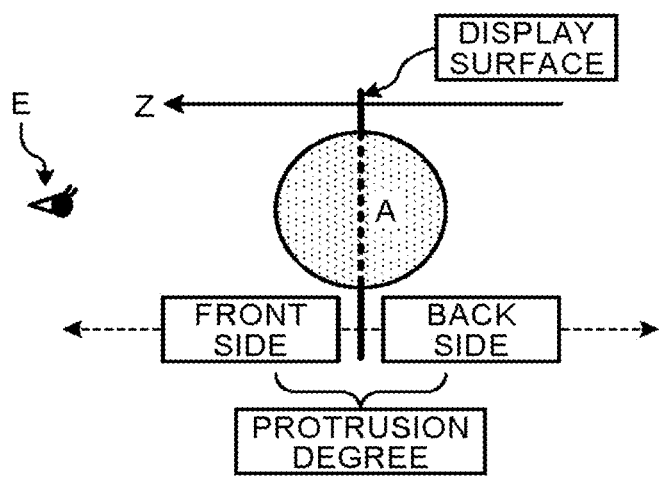
FIG. 10 is a diagram that illustrates the stereoscopic image space according to the first embodiment.

Here, the degree of protrusion is explained by using FIG. 10. FIG. 10 is a diagram that illustrates the stereoscopic image space according to the first embodiment. As illustrated in FIG. 10, when seeing the parallax image group that is displayed on the stereoscopic display monitor, an observer views a stereoscopic image A in the stereoscopic image space in three dimensions. Here, the appearance of solidity that is sensed by the observer is broadly divided into the appearance of solidity on the front side (also referred to as the sense of protrusion) and the appearance of solidity on the back side (also referred to as the sense of depth), as illustrated in FIG. 10. The appearance of solidity on the front side is the sense that is perceived by the observer such that the stereoscopic image is protruded in the direction from the display surface of the stereoscopic display monitor toward the viewpoint (an observer's viewpoint E) of the observer. Furthermore, the appearance of solidity on the back side is the sense that is perceived by the observer such that the stereoscopic image is set back in the direction from the display surface of the stereoscopic display monitor and away from the viewpoint (the observer's viewpoint E) of the observer.

Thus, during observation of stereoscopic images on the stereoscopic display monitor, the appearance of solidity on the front side and the appearance of solidity on the back side are perceived in a direction (Z direction) perpendicular to the display surface of the stereoscopic display monitor. The above-described degree of protrusion indicates the length that is a combination of the length that corresponds to the appearance of solidity on the front side and the length that corresponds to the appearance of solidity on the back side, as illustrated in FIG. 10. Here, the maximal value of the degree of protrusion is defined for each system (stereoscopic display monitor).

The reconstructing circuitry 1352 adjusts the parallactic angle during generation of the parallax image group such that the degrees of protrusion of the medical images are matched when the medical images are stereoscopically viewed. For example, to increase the degree of protrusion, the reconstructing circuitry 1352 controls the rendering processing circuitry 136 so as to generate a parallax image group with a larger parallactic angle. Conversely, to decrease the degree of protrusion, the reconstructing circuitry 1352 controls the rendering processing circuitry 136 so as to generate a parallax image group with a smaller parallactic angle. As for the degree of protrusion, there may be a case where the largest degree of protrusion of the stereoscopic display monitor is preset, or there may be a case where it is optionally set by an operator. For example, the reconstructing circuitry 1352 controls the rendering processing circuitry 136 so as to adjust the parallactic angle such that the degree of protrusion is "4 cm" when each parallax image group is generated from the volume data on each medical image that is illustrated in FIG. 9 and perform a volume rendering operation with the adjusted parallactic angle.

The display control circuitry 1353 causes the display 132 to display the parallax image group that is generated by the rendering processing circuitry 136 after the parallactic angle is adjusted such that the degree of protrusion is matched with regard to each volume data that is reconstructed by the reconstructing circuitry 1352. At this point, as the resolution, in the XY direction, of each volume data that is processed by the rendering processing circuitry 136 is the same, the size of the site of interest, displayed by the display 132, is identical. Furthermore, as the parallax image group is generated with the parallactic angle that is adjusted such that the degree of protrusion is matched, the size (the appearance of solidity) in the Z direction is also the same. Therefore, the workstation 130 according to the first embodiment may display an easily observable medical image in a stable manner.

Furthermore, the example illustrated in FIG. 9 is only an example, and this is not a limitation on the embodiment. For example, there may be a case where the X-ray image, acquired by the X-ray diagnostic apparatus, is used as the target volume data. Furthermore, in the above-described example, an explanation is given of a case where the slice thickness is used as the Z-direction resolution of each volume data except the ultrasonic image; however, this is not a limitation on the embodiment and, for example, there may be a case where the reconstruction interval is used as indicated by the image information on the CT image of FIG. 9. For example, if the value of the reconstruction interval is smaller than the value of the slice thickness, the reconstruction interval may be used as the Z-direction resolution.

Furthermore, there may be a case where the image is displayed such that the size of the displayed image is matched to the actual size. For example, there may be a case where, if the head size is 20 cm, it is displayed with the size of 20 cm on the screen regardless of the resolution. In such a case, for example, the display control circuitry 1353 causes the display 132 to display the stereoscopic image in the actual size. For instance, the display control circuitry 1353 acquires the size of the display 132 (monitor) and calculates the size of 1 pixel of the monitor from the acquired monitor size. Then, on the basis of the calculated size, the display control circuitry 1353 displays a stereoscopic image in accordance with the actual size. That is, the display control circuitry 1353 causes the display 132 to display the images of various medical-image diagnostic apparatus (modality) with the actual size. Furthermore, the storage circuitry 134 previously stores the information on the actual size of each site, and the display control circuitry 1353 acquires, from the storage circuitry 134, the actual size of the site that is equivalent to the site to be displayed as the stereoscopic image. Alternatively, for example, there may be a case where, on the basis of the size of the monitor, the rendering processing circuitry 136 performs a rendering operation such that the stereoscopic image is displayed in the actual size. As described above, as the resolutions are matched, the data on various modalities may be easily superimposed and displayed (fusion) simultaneously.

An explanation is given below of a case where fusion is conducted on the medical images of multiple modalities. In such a case, for example, the reconstructing circuitry 1352 reconstructs volume data with regard to each medical image as described above and, in the reconstructed volume data, sets the area to be displayed as the stereoscopic image. That is, the reconstructing circuitry 1352 sets the area such that the data size is matched so that the parallax image group, generated from the volume data on each medical image, is fused in three dimensions. Then, the reconstructing circuitry 1352 controls the rendering processing circuitry 136 so as to generate each parallax image group from the volume data on the set area. Here, the reconstructing circuitry 1352 causes a rendering operation to be performed by adjusting the parallactic angle such that the degree of protrusion of each medical image becomes the same.

FIG. 11 is a diagram that illustrates an example of the fusion of the stereoscopic image according to the first embodiment. For example, as illustrated in FIG. 11(A), the reconstructing circuitry 1352 reconstructs each volume data with regard to the MR image in which a nerve fiber is captured by using the nerve fiber tractography, the CT image in which a bone is captured by using simple radiography, the CT image in which a blood vessel is captured by using CTA (CT-Angio), and the PET image in which a tumor is captured by using FDG (fluorodeoxyglucose), and sets the size "320 mm×320 mm×320 mm" to the reconstructed volume data. That is, the reconstructing circuitry 1352 causes a volume rendering operation to be performed on the volume data of the size "320 mm×320 mm×320 mm" so that a parallax image group is generated. At this point, as illustrated in FIG. 11(B), the reconstructing circuitry 1352 causes the parallactic angle to be adjusted such that 4 sets of data have the same degree of protrusion and causes a volume rendering operation to be performed. Furthermore, there may be a case where the degree of protrusion is preset, or there may be a case where it is set by an operator.

The display control circuitry 1353 causes the display 132, which is the stereoscopic display monitor, to display a fusion image that is a fusion of a plurality of parallax image groups, generated under the control of the reconstructing circuitry 1352. Thus, it is possible to observe a stereoscopic image that is fused in three dimensions with respect to the medical images of multiple modalities. Here, although the fusion image is displayed as described above, the medical images that are acquired by the modalities have different resolution performances. Therefore, for example, if the degree of protrusion is matched in accordance with the medical image that has the highest resolution performance, the image quality of the medical image with the lowest resolution performance is sometimes degraded (for example, an edge portion is sometimes blurred on the protruded front side or back side).

Therefore, the workstation 130 according to the first embodiment adjusts the parallactic angle depending on the resolution performance of the medical image. Specifically, with regard to the volume data that is acquired by each of the multiple types of medical-image diagnostic apparatus, the reconstructing circuitry 1352 controls the rendering processing circuitry 136 so as to adjust each parallactic angle during generation of a parallax image group in accordance with the resolution performance in the direction that corresponds to the screen direction for display on the display 132, which is the stereoscopic display monitor, and generate each parallax image group on the basis of the volume data that is acquired by each of the multiple types of medical-image diagnostic apparatus in accordance with each of the adjusted parallactic angles. For example, the reconstructing circuitry 1352 adjusts the parallactic angle in accordance with the degree of protrusion that is suitable for the medical image with the lowest resolution performance among the acquired medical images. Thus, it is possible to observe the fusion image with which the image qualities of all the medical images are not degraded.

Furthermore, the workstation 130 according to the first embodiment may also change the protrusion position of a stereoscopic image. As described above, a stereoscopic image has the appearance of solidity in the direction from the display surface of the stereoscopic display monitor toward the observer's viewpoint and in the direction from the display surface of the stereoscopic display monitor and away from the observer's viewpoint. That is, a stereoscopic image has the appearance of solidity on the front side and the back side with the display surface of the stereoscopic display monitor as a reference surface. The workstation 130 may display a stereoscopic image by setting not only the display surface of the stereoscopic display monitor as the reference surface but also the front side or the back side of the display surface of the stereoscopic display monitor as the reference surface. In other words, the workstation 130 may change the position of the stereoscopic image in a vertical direction (the Z direction) relative to the display surface of the stereoscopic display monitor.

FIG. 12 is a diagram that illustrates an example of the operation to change the protrusion position by the reconstructing circuitry 1352 according to the first embodiment. Here, FIG. 12 illustrates a case where the protrusion position of the four sets of data, illustrated in FIG. 11, is changed. For example, as illustrated in FIG. 12(A), the reconstructing circuitry 1352 constructs virtual volume data, wherein the four sets of volume data, whose area is specified, are allocated in the virtual space. Here, if the reference surface of the stereoscopic image is set on the front side of the display surface, the reconstructing circuitry 1352 allocates the four sets of data on the front side in the Z direction of the virtual space. Conversely, if the reference surface of the stereoscopic image is set on the back side of the display surface, the reconstructing circuitry 1352 allocates the four sets of data on the back side in the Z direction of the virtual space. For example, as illustrated in FIG. 12(A), if a parallax image group is generated in a state such that the four sets of data are allocated on the front side of the virtual space, the display 132 displays a fusion image where the four sets of data are represented on the front side of the display surface, as illustrated in FIG. 12(B).

Here, the reconstructing circuitry 1352 adjusts the parallactic angle during generation of a parallax image group from the virtual volume data where the four sets of volume data are allocated, thereby adjusting the degrees of protrusion of the four sets of data. Furthermore, although an explanation is given, in the example illustrated in FIG. 12, of a case where the protrusion position of the four sets of data is changed, the protrusion position of the number of sets of data other than four may be changed in the same manner.

In the above-described example, an explanation is given of a case where a fusion image is displayed, for which the degrees of protrusion are matched with regard to multiple medical images; however, this is not a limitation on the embodiment, and it may be individually set for each medical image. For example, the workstation 130 may set the degree of protrusion and the protrusion position of the medical image that needs to be intensively observed, differently from the other medical images.

FIG. 13 is a diagram that illustrates an example of the control by the workstation 130 according to the first embodiment. Here, FIG. 13 illustrates a case where the control is performed on the single data among the four sets of data that are illustrated in FIG. 11. For example, the workstation 130 changes the settings of the specific data among the four sets of data that are illustrated in FIG. 13(A), thereby generating and displaying a fusion image where the single data is displayed differently from the other three sets of data as illustrated in FIG. 13(B). An explanation is given below of an example where, among the MR image in which a nerve fiber is captured, the CT image in which a bone is captured, the CT image in which a blood vessel is captured, and the PET image in which a tumor is captured, the MR image with the low resolution performance is individually set so that an easily observable fusion image is displayed.

In such a case, for example, the reconstructing circuitry 1352 decreases the parallactic angle without changing the specified area in the volume data on the MR image so as to reduce the degree of protrusion, thereby generating an easily observable parallax image group for the MR image. Here, the reconstructing circuitry 1352 changes the protrusion position to correct the position of the area of interest, which is changed due to a decrease in the degree of protrusion. For example, the reconstructing circuitry 1352 calculates the amount of change of the area of interest that is changed due to a decrease in the degree of protrusion. Then, to allocate the volume data on the MR image in the virtual space, the reconstructing circuitry 1352 moves it by an equivalence of the calculated amount of change and allocates it. Then, the reconstructing circuitry 1352 causes a volume rendering operation to be performed on the virtual volume data, where the volume data on the MR image is allocated, with the reduced parallactic angle so that the parallax image group of the MR image is generated.

Furthermore, for example, the reconstructing circuitry 1352 changes the area that is specified in the volume data on the MR image without changing the degree of protrusion, thereby generating an easily observable parallax image group with regard to the MR image. Specifically, the reconstructing circuitry 1352 performs a control so as to change the area such that it includes only the area of interest in the MR image, thereby generating a more easily observable parallax image group in which other than the area of interest in the MR image is not rendered. In such a case, the reconstructing circuitry 1352 specifies, as the area, the region that includes the area of interest in the volume data on the MR image. Here, the reconstructing circuitry 1352 allocates the volume data on the area of interest at the position where the area of interest is originally located in the virtual space that has the same size as the size of the area of other volume data. Then, the reconstructing circuitry 1352 causes a volume rendering operation to be performed on the virtual volume data, in which the volume data on the area of interest is allocated, with the parallactic angle such that the degree of protrusion is the same as those of the other medical images, whereby the parallax image group on the MR image is generated.

As described above, the workstation 130 may generate and display a fusion image in which the area of interest in a predetermined medical image is observable more easily. Here, as the method for facilitating observation of the area of interest, the workstation 130 may implement methods other than the above-described method of changing the area. Specifically, the workstation 130 deletes the area other than the area of interest in a predetermined medical image by using a mask image, thereby facilitating observation of the area of interest.

In such a case, for example, the reconstructing circuitry 1352 specifies the same area in the volume data on the MR image as the other medical images. Here, the reconstructing circuitry 1352 acquires the information about the area other than the area of interest in the volume data on the MR image and subtracts the area that corresponds to the information that is acquired from the volume data, thereby generating the volume data that contains little other than the area of interest. Then, the reconstructing circuitry 1352 uses the generated volume data to generate a parallax image group with the parallactic angle with which the degree of protrusion becomes the same. Furthermore, the information about the area other than the area of interest in the volume data on the MR image is input by, for example, an operator via the input circuitry 131.

In this way, the workstation 130 may change various settings with regard to an arbitrary medical image among multiple medical images. Here, these changes may be made by an operator, who observes the fusion image, via a GUI, or the like, in a flexible manner. Specifically, while an operator observes a fusion image, the operator may select an arbitrary medical image and change various settings for the selected medical image. For example, while the operator observes a fusion image, the operator may operate a mouse, trackball, or the like, to select an arbitrary medical image included in the fusion image and change the degree of protrusion or specify an area other than the area of interest to delete the specified area other than the area of interest.

Furthermore, for example, if the fusion image is moved by an operator while it is observed and the extreme end of the area is reached, a farther region may also be specified again as the area so that a fusion image is generated and displayed again. For example, if 320 mm×320 mm×320 mm is specified as the area from the entire volume data of 500 mm×500 mm×500 mm, the area at the position beyond 320 mm may also be specified again so that a fusion image is generated and displayed again.

Furthermore, while the fusion image of the four sets of data is displayed, new data of interest may also be displayed. In such a case, the reconstructing circuitry 1352 allocates the volume data, acquired by each of the multiple types of medical-image diagnostic apparatus, in a first position and a second position in the virtual space, performs a volume rendering operation in a state such that each positional information is retained, and generates a plurality of parallax image groups on the basis of each volume data. Then, the display control circuitry 1353 causes the display 132, which is the stereoscopic display monitor, to display a plurality of parallax image groups that are generated by the reconstructing circuitry 1352, thereby displaying the stereoscopic image where the fusion images are allocated in the positions that correspond to the first position and the second position in the depth direction of the stereoscopic display monitor.

For example, the reconstructing circuitry 1352 allocates the volume data of the four sets of data, which is previously observed, on the back side of the virtual space and allocates the volume data on the area of interest, which is set by an operator, on the front side of the same virtual space. Then, the reconstructing circuitry 1352 generates each parallax image group from the virtual volume data where each volume data is allocated in the virtual space. Here, the reconstructing circuitry 1352 adjusts each parallactic angle during generation of the parallax image group, thereby adjusting the degree of protrusion of the fusion image of the four sets of data and the degree of protrusion of the area of interest. Then, the display control circuitry 1353 displays each of the generated parallax image groups on a different layer, whereby the fusion image of the previously observed four sets of data is displayed on the back side of the stereoscopic display monitor, and the stereoscopic image of the area of interest is displayed on the front side.

Furthermore, the above-described example is only an example, and this is not a limitation on the embodiment. For example, the previously observed fusion image of the four sets of data and the fusion image of further different four sets of data may also be displayed in the depth direction of the stereoscopic display monitor. Furthermore, if multiple stereoscopic images are displayed in the depth direction of the stereoscopic display monitor, as described above, the opacity of the stereoscopic image on the front side is adjusted. Furthermore, the images that are displayed in the depth direction of the stereoscopic display monitor are not limited to the images that are acquired by medical-image diagnostic apparatus, and there may be a case where different image data is used. Specifically, the display control circuitry 1353 causes the model image that corresponds to the parallax image group to be displayed on the front side or the back side of the parallax image group relative to the stereoscopic display monitor. FIG. 14 is a diagram that illustrates an example of the stereoscopic image according to the first embodiment.

For example, as illustrated in FIG. 14, the workstation 130 may also display anatomy data in the textbook on the back side of the fusion image of the four sets of data. In such a case, for example, the reconstructing circuitry 1352 allocates the anatomy data in the textbook on the back side of the virtual space and allocates the volume data of the four sets of data on the front side, as described above. Then, the reconstructing circuitry 1352 causes each parallax image group to be generated from the virtual volume data, in which each volume data is allocated, with the set parallactic angle. The display control circuitry 1353 causes the generated parallax image group to be displayed on a different layer, whereby the anatomy data in the textbook is displayed on the back side of the display surface and the fusion image of the four sets of data is displayed on the front side of the display surface, as illustrated in FIG. 14(B).

As described above, the workstation 130 may receive various operations from the operator and change the stereoscopic image that is displayed on the display 132. Here, if the above-described multimodality medical images are displayed, the workstation 130 may provide the automatic mode for displaying with the preset condition of the degree of protrusion, the protrusion position, or the like, and the edition mode with which changes may be made by the operator in a flexible manner. For example, when the application of the multimodality is activated, the workstation 130 displays the screen for selecting the automatic mode or the edition mode and causes the operator to make a selection.

Here, if the edition mode is selected, the workstation 130 receives various changes as described above and displays the stereoscopic image in accordance with the received change. Conversely, if the automatic mode is selected, the workstation 130 displays the stereoscopic image with the preset condition. In such a case, for example, the storage circuitry 134 relates the image, the site, or the like, which is displayed as a fusion image, to a condition and stores them. The reconstructing circuitry 1352 reads the condition that corresponds to the image information, acquired by the image-information acquiring circuitry 1351, and generates a fusion image with the read condition.

Furthermore, for example, the degree of protrusion or the protrusion position of each medical image, the area in volume data, or the like, are related as the condition; however, these conditions may be optionally set by an operator, and a unique condition may also be set by each operator. Furthermore, the workstation 130 may also learn the set condition and update the information that is stored in the storage circuitry 134. Here, the related conditions are not only the degree of protrusion or the protrusion position, and the setting may be also made such that only a predetermined medical image is displayed in the edition mode. That is, if the fusion image of the four sets of data is displayed, only a predetermined medical image among the four is displayed in the edition mode.

Figure 15:
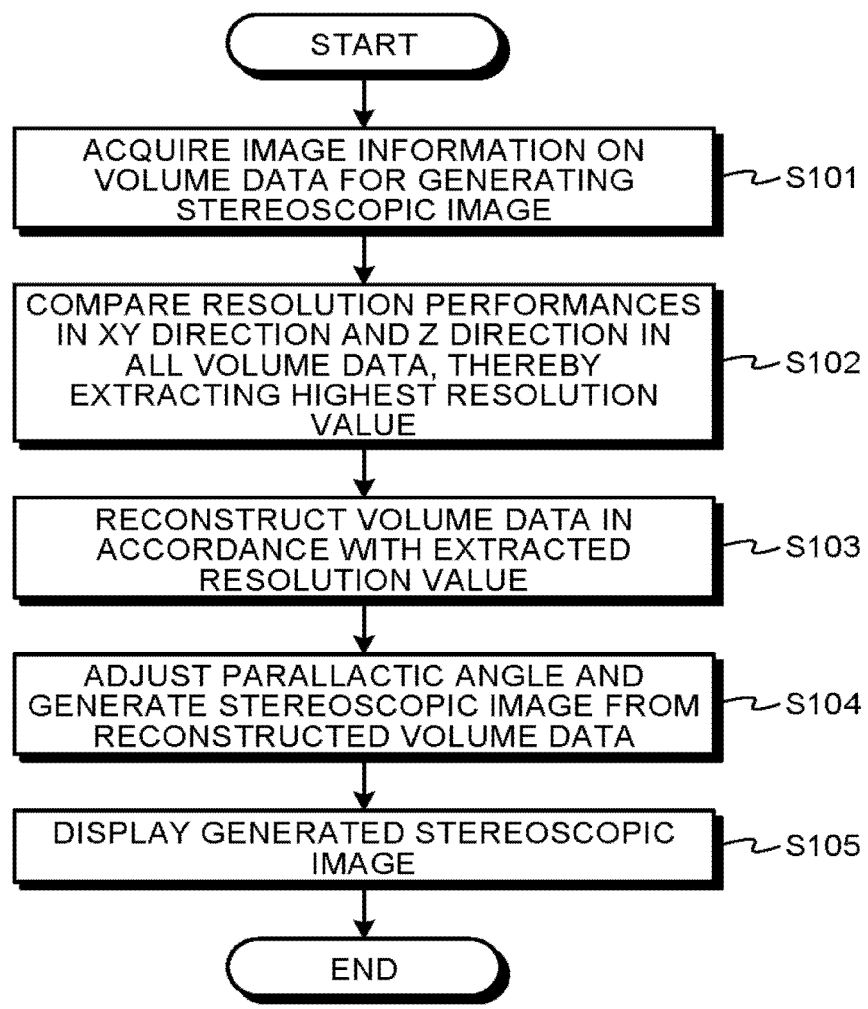
FIG. 15 is a flowchart that illustrates the steps of the operation by the workstation according to the first embodiment.

Next, by using FIG. 15, an explanation is given of an operation of the workstation 130 according to the first embodiment. FIG. 15 is a flowchart that illustrates the steps of the operation by the workstation 130 according to the first embodiment. As illustrated in FIG. 15, in the workstation 130 according to the first embodiment, for example, when the input circuitry 131 receives an operation for displaying the stereoscopic image from the operator, the image-information acquiring circuitry 1351 acquires the image information on the volume data for generating the stereoscopic image (Step S101).

Then, the reconstructing circuitry 1352 compares the resolution performances in the XY direction and the Z direction in all the volume data, thereby extracting the highest resolution value (Step S102). Then, the reconstructing circuitry 1352 reconstructs volume data in accordance with the extracted resolution value (Step S103).

Next, the reconstructing circuitry 1352 adjusts the parallactic angle, and the rendering processing circuitry 136 generates the stereoscopic image (the parallax image group) with the adjusted parallactic angle by using the volume data that is reconstructed by the reconstructing circuitry 1352 (Step S104). Then, the display control circuitry 1353 causes the display 132 to display the stereoscopic image that is generated by the rendering processing circuitry 136 (Step S105).

As described above, according to the first embodiment, the image-information acquiring circuitry 1351 acquires the image information on the volume data for displaying the stereoscopic image on the stereoscopically viewable display 132. Then, the reconstructing circuitry 1352 reconstructs the resolution of the volume data into a predetermined resolution on the basis of the image information on the volume data that is acquired by the image-information acquiring circuitry 1351. The display control circuitry 1353 causes the display 132 to display the stereoscopic image that is generated by using the volume data that is reconstructed into the predetermined resolution by the reconstructing circuitry 1352. Therefore, the workstation 130 according to the first embodiment may generate a stereoscopic image by using volume data that is matched with the predetermined resolution and may display an easily observable medical image in a stable manner.

Furthermore, according to the first embodiment, the reconstructing circuitry 1352 uses, as the predetermined resolution, the highest value among the resolutions that are included in the image information on the volume data, acquired by the image-information acquiring circuitry 1351. Therefore, the workstation 130 according to the first embodiment may generate a stereoscopic image in accordance with the best resolution and may display a more easily observable medical image in a stable manner.

Furthermore, according to the first embodiment, the display control circuitry 1353 displays a stereoscopic image in the actual size on the display 132. Therefore, the workstation 130 according to the first embodiment may display stereoscopic images by setting the images of various modalities in the actual size and may display more easily observable medical images.

Second Embodiment

In the first embodiment, an explanation is given of a case where the size of a medical image is matched in accordance with the resolution of volume data and is displayed. In a second embodiment, an explanation is given of a case where volume data is reconstructed in accordance with the size of the display for display. Here, compared with the first embodiment, the second embodiment is different in only the operation of the reconstructing circuitry 1352. An explanation is primarily given below on this.

The reconstructing circuitry 1352 according to the second embodiment reconstructs the resolution of medical image data into a predetermined resolution on the basis of the screen resolution of the display in addition to the image information on the medical image data, acquired by the image-information acquiring circuitry 1351. Specifically, the reconstructing circuitry 1352 reconstructs volume data in accordance with the area (effective stereoscopic display area) where the stereoscopic image may be effectively displayed on the display 132.

Figure 16:
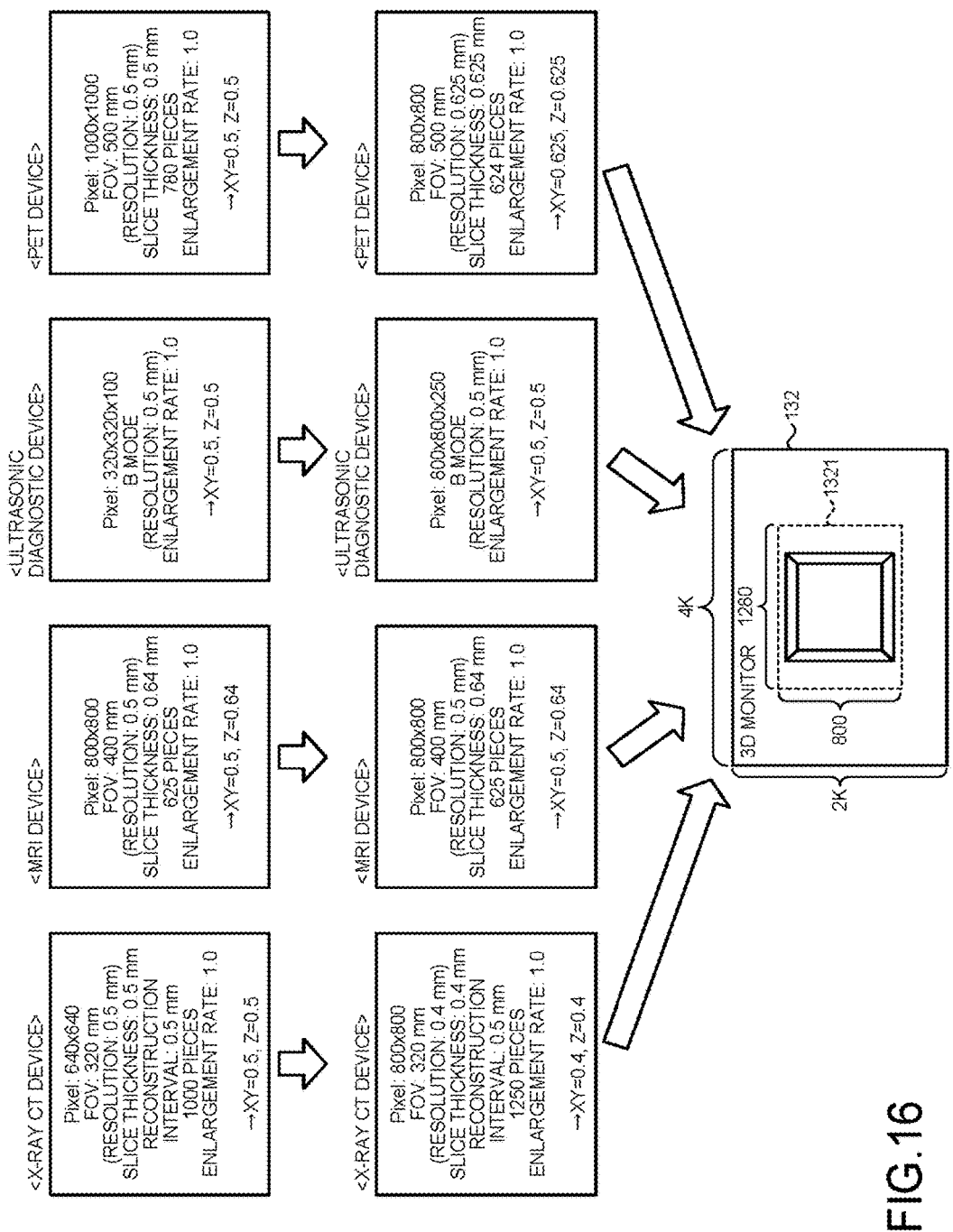
FIG. 16 is a diagram that illustrates an example of the operation by the workstation according to a second embodiment.

FIG. 16 is a diagram that illustrates an example of the operation by the workstation 130 according to the second embodiment. FIG. 16 illustrates a case where the display 132 has the resolution of 4K2K (e.g., 4096×2160 or 3840× 2160) and the effective stereoscopic display area is "1280× 800". Furthermore, the example illustrated as 4K2K is only an example, and this is not a limitation on the embodiment. Here, the information, such as the resolution of the display 132 or the effective stereoscopic display area, is previously stored in the storage circuitry 134. Furthermore, FIG. 16 illustrates the operation after the reconstruction of volume data is conducted by using the resolution that is illustrated in FIG. 9.

For example, the reconstructing circuitry 1352 acquires, from the storage circuitry 134, the information on the effective stereoscopic display area on the display 132 that displays a stereoscopic image and reconstructs volume data in accordance with the acquired effective stereoscopic display area. For example, the reconstructing circuitry 1352 first acquires the effective stereoscopic display area "1280×800" of the display 132. Then, for example, if the medical image whose stereoscopic image is to be displayed is a CT image, the size of the volume data on the CT image in the X direction and the Y direction is the same (square); therefore, the reconstructing circuitry 1352 determines that, of the effective stereoscopic display area "1280×800", the smaller value "800" is a reference. Specifically, if the larger value "1280" is a reference, the X direction is included in the effective stereoscopic display area, although the Y direction deviates from the effective stereoscopic display area; thus, the reconstructing circuitry 1352 prevents the above-described deviation.

Then, the reconstructing circuitry 1352 reconstructs the volume data on the CT image from "Pixel: 640×640" into the determined "800×800". Specifically, as illustrated in FIG. 11, the reconstructing circuitry 1352 enlarges the volume data on the CT image into "Pixel: 800×800" and reconstructs it as "FOV: 320 mm", "resolution: 0.4 (=0.5/800/640)", "slice thickness: 0.4 mm", "reconstruction interval: 0.5 mm", "1250 pieces (=1000×800/640)", "enlargement rate: 1.0", "XY=0.4", and "Z=0.4 mm". Furthermore, the value that is designated by the operator is acquired as the above-described enlargement rate.

Furthermore, for example, the reconstructing circuitry 1352 does not reconstruct the volume data on the MR image but sets the data without change as it is "Pixel: 800×800".

Furthermore, for example, the reconstructing circuitry 1352 enlarges the volume data on the ultrasonic image into "Pixel: 800×800×250 (=100×800/320)" and reconstructs it as "B mode resolution: 0.5", "enlargement rate: 1.0", "XY=0.5", and "Z=0.5 mm". Here, the value that is designated by the operator is acquired as the above-described enlargement rate.

Furthermore, for example, the reconstructing circuitry 1352 reduces the volume data on the PET image into "Pixel: 800×800" and reconstructs it as "FOV: 500 mm", "resolution: 0.625 (=0.5/800/1000)", "slice thickness: 0.625 mm", "624 pieces (=780×800/1000)", "enlargement rate: 1.0", "XY=0.625", and "Z=0.625 mm". Here, the value that is designated by the operator is acquired as the above-described enlargement rate.

As described above, the reconstructing circuitry 1352 reconstructs volume data in accordance with the effective stereoscopic display area of the display 132, whereby the stereoscopic image, which is displayed under the control of the display control circuitry 1353, becomes the image that is matched with an effective stereoscopic display area 1321 of the display 132, as illustrated in FIG. 16. Therefore, the workstation 130 according to the second embodiment may display easily observable medical images in a stable manner.

Figure 17:
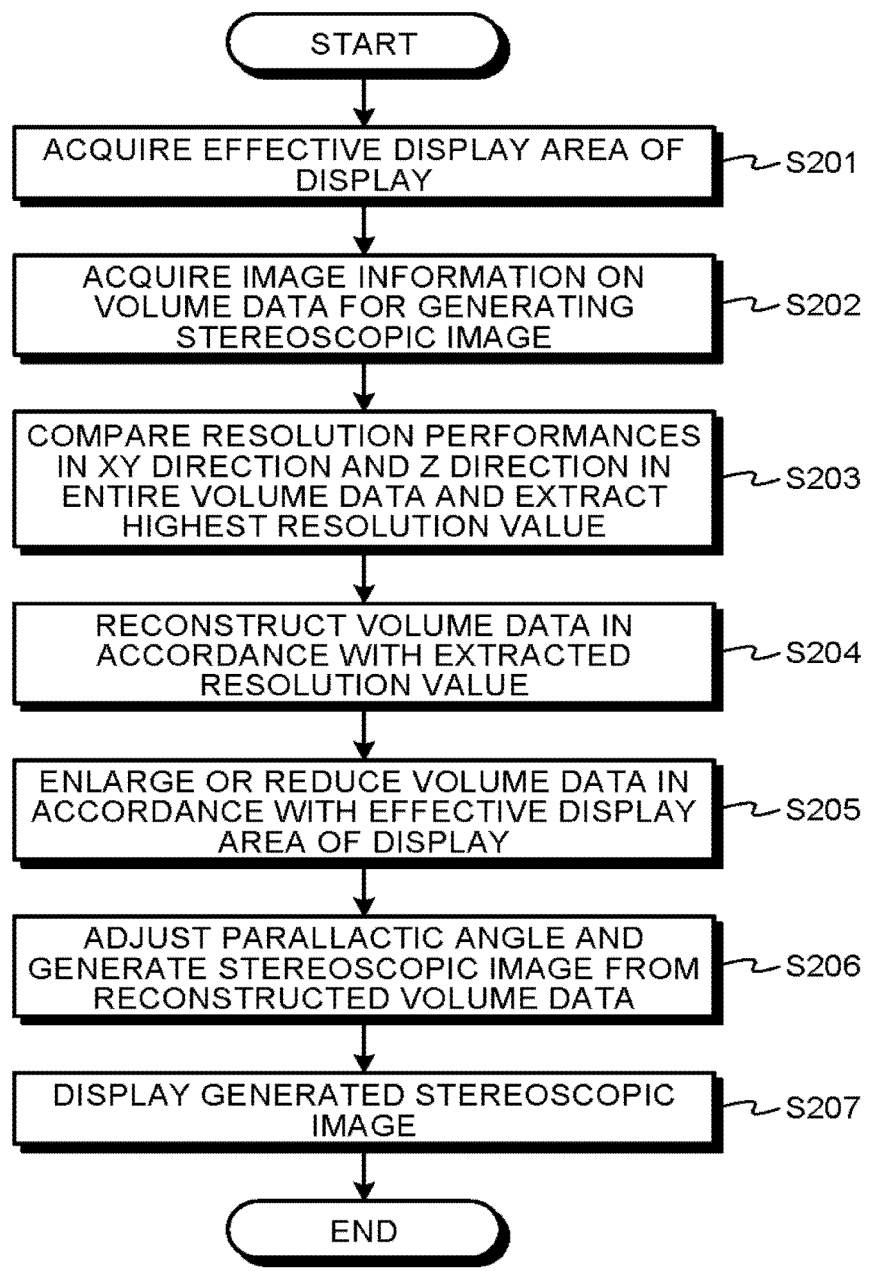
FIG. 17 is a flowchart that illustrates the steps of the operation by the workstation according to the second embodiment.

Next, an explanation is given of an operation of the workstation 130 according to the second embodiment by using FIG. 17. FIG. 17 is a flowchart that illustrates the steps of the operation by the workstation 130 according to the second embodiment. As illustrated in FIG. 17, in the workstation 130 according to the second embodiment, for example, when the input circuitry 131 receives an operation to display a stereoscopic image from the operator, the reconstructing circuitry 1352 acquires the information on the effective stereoscopic display area of the display 132 (Step S201). Then, the image-information acquiring circuitry 1351 acquires the image information on the volume data for generating the stereoscopic image (Step S202).

Then, the reconstructing circuitry 1352 compares the resolution performances in the XY direction and the Z direction in the entire volume data and extracts the highest resolution value (Step S203). Then, the reconstructing circuitry 1352 reconstructs the volume data in accordance with the extracted resolution value (Step S204). Furthermore, the reconstructing circuitry 1352 further enlarges or reduces the volume data in accordance with the acquired effective stereoscopic display area (Step S205).

Next, the reconstructing circuitry 1352 adjusts the parallactic angle, and the rendering processing circuitry 136 generates a stereoscopic image (parallax image group) with the adjusted parallactic angle by using the volume data that is reconstructed by the reconstructing circuitry 1352 (Step S206). Then, the display control circuitry 1353 causes the display 132 to display the stereoscopic image that is generated by the rendering processing circuitry 136 (Step S207).

As described above, according to the second embodiment, the reconstructing circuitry 1352 reconstructs the resolution of the volume data into a predetermined resolution in accordance with the effective stereoscopic display area of the display 132 in addition to the image information on the volume data that is acquired by the image-information acquiring circuitry 1351. Therefore, the workstation 130 according to the second embodiment makes it possible to display more easily observable medical images in a stable manner.

Third Embodiment

The workstation 130 according to the present application may also adjust the sense of depth by enlargement or reduction in the Z direction. In a third embodiment, an explanation is given of a case where the sense of depth of the generated stereoscopic image is adjusted based on "XY" and "Z" of the volume data. According to the third embodiment, only the operation of the reconstructing circuitry 1352 is different. An explanation is primarily given below of this.

In accordance with the size of the medical image data, acquired by the image-information acquiring circuitry 1351, the reconstructing circuitry 1352 according to the third embodiment enlarges or reduces the stereoscopic image that is generated from the medical image data. For example, the reconstructing circuitry 1352 enlarges or reduces the stereoscopic image in the depth direction in accordance with the size of the medical image data, acquired by the image-information acquiring circuitry 1351, in the depth direction. For example, as for the values of "XY" and "Z" of the volume data, acquired by the image-information acquiring circuitry 1351, if "XY"<"Z", the reconstructing circuitry 1352 reduces the stereoscopic image in the depth direction.

Here, the reconstructing circuitry 1352 reduces the stereoscopic image in the depth direction, for example, on the basis of the previously set reduction rate. FIG. 18 is a diagram that illustrates an example of the adjustment information in the depth direction, which is referred to by the reconstructing circuitry 1352 according to the third embodiment. Here, "size" in FIG. 18 indicates the information on the comparison between the size of "XY" and the size of "Z". Furthermore, "sense of depth" in FIG. 13 indicates the enlargement rate (the reduction rate) in the axis-Z direction relative to the axis-X direction and the axis-Y direction in the stereoscopic image. Furthermore, the information that is illustrated in FIG. 18 is previously set and stored in the storage circuitry 134.

For example, as illustrated in FIG. 18, the storage circuitry 134 stores the adjustment information that is the depth information, in which "size: XY<1.2Z" is related to "sense of depth: 1:1:0.8". The above-described information means that the sense of depth of a stereoscopic image is set to "0.8-fold" if the size of the volume data in "Z" exceeds "1.2"-fold of the size in "XY". In the same manner, various types of adjustment information are stored depending on the sizes.

For example, the reconstructing circuitry 1352 refers to the value of "XY" of the volume data, the value of "Z", and the adjustment information on the depth direction, thereby adjusting the sense of depth of the stereoscopic image that is generated by the rendering processing circuitry 136. For example, the reconstructing circuitry 1352 determines that "XY<Z" from "XY=0.5" and "Z=0.64" of the MR image that is illustrated in FIG. 16 and calculates that the value of "Z" is "1.28-fold=(0.64/0.5)" of the value of "XY". Then, the reconstructing circuitry 1352 refers to the adjustment information on the depth direction and extracts "size: XY<1.2Z, sense of depth: 1:1:0.8" that corresponds to the calculated "1.28-fold". Then, the reconstructing circuitry 1352 causes the rendering processing circuitry 136 to generate the stereoscopic image that corresponds to the extracted adjustment information. That is, the stereoscopic image with the "0.8-fold" sense of depth is generated.

Furthermore, in the above-described example, an explanation is given of a case where reduction is conducted in the depth direction; however, this is not a limitation on the embodiment and, for example, if "XY>Z", enlargement may be conducted in the depth direction. Furthermore, there may be a case where, in addition to enlargement and reduction in the depth direction, enlargement or reduction may be conducted in the vertical direction and the horizontal direction. Furthermore, the adjustment information that is illustrated in FIG. 18 is only an example, and this is not a limitation. That is, the storage circuitry 134 stores not only the information for reduction in the depth direction but also each adjustment information depending on the adjustment of the stereoscopic image to be generated.

Figure 19:
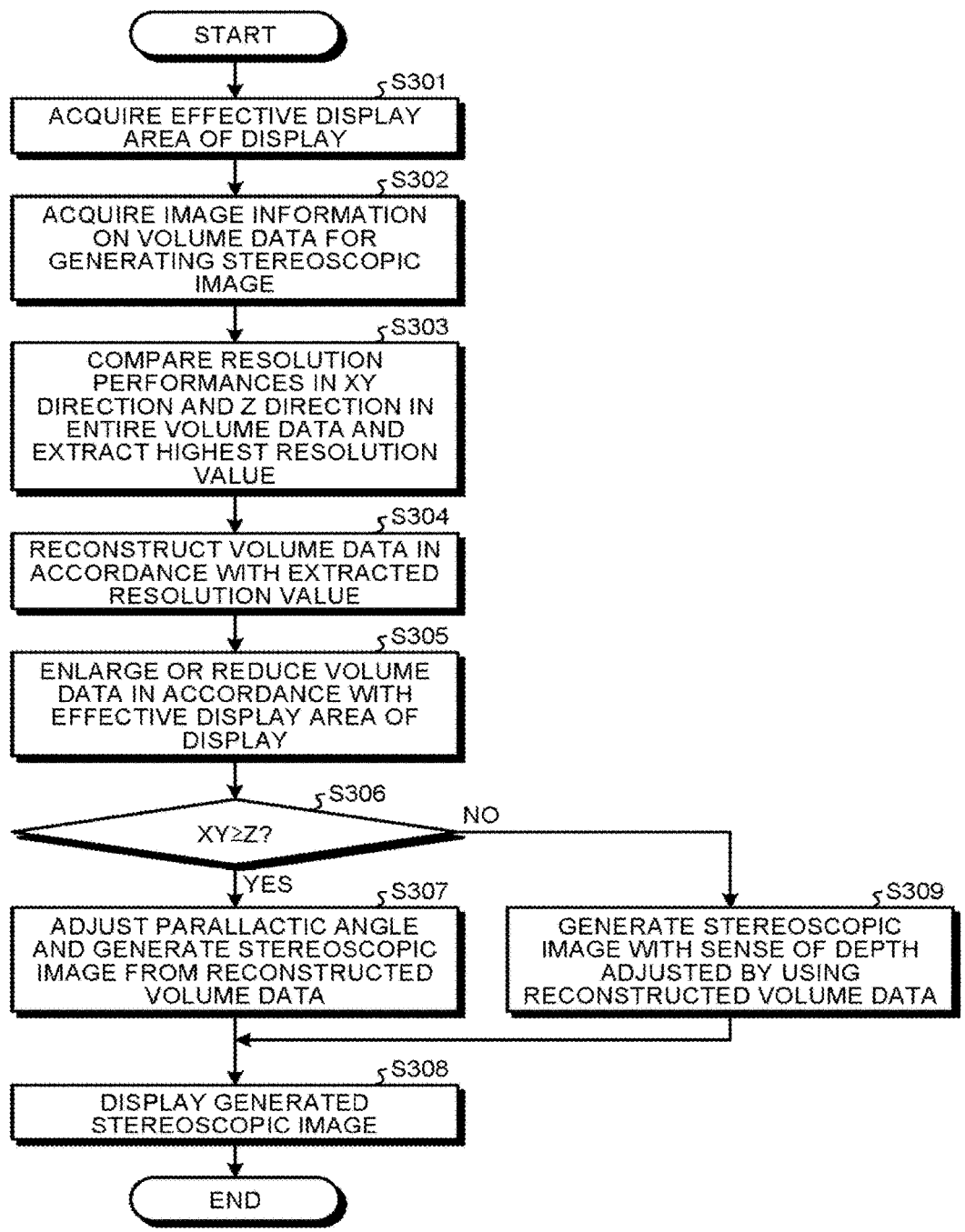
FIG. 19 is a flowchart that illustrates the steps of the operation by the workstation according to the third embodiment.

Next, an explanation is given of an operation of the workstation 130 according to the third embodiment by using FIG. 19. FIG. 19 is a flowchart that illustrates the steps of the operation by the workstation 130 according to the third embodiment. As illustrated in FIG. 19, in the workstation 130 according to the third embodiment, for example, when the input circuitry 131 receives an operation to display the stereoscopic image from the operator, the reconstructing circuitry 1352 acquires the information on the effective stereoscopic display area of the display 132 (Step S301). Then, the image-information acquiring circuitry 1351 acquires the image information on the volume data for generating the stereoscopic image (Step S302).

Then, the reconstructing circuitry 1352 compares the resolution performances in the XY direction and the Z direction in the entire volume data and extracts the highest resolution value (Step S303). Then, the reconstructing circuitry 1352 reconstructs the volume data in accordance with the extracted resolution value (Step S304). Furthermore, the reconstructing circuitry 1352 further enlarges or reduces the volume data in accordance with the acquired effective stereoscopic display area (Step S305).

Afterward, the reconstructing circuitry 1352 determines whether the volume data is "XY≥Z" (Step S306). Here, if the volume data is "XY≥Z" (Yes at Step S306), the reconstructing circuitry 1352 causes the rendering processing circuitry 136 to perform a rendering operation on the reconstructed volume data without change.

Specifically, the reconstructing circuitry 1352 adjusts the parallactic angle, the rendering processing circuitry 136 generates a stereoscopic image (parallax image group) with the adjusted parallactic angle by using the volume data that is reconstructed by the reconstructing circuitry 1352 (Step S307), and the display control circuitry 1353 causes the display 132 to display the stereoscopic image that is generated by the rendering processing circuitry 136 (Step S308).

Conversely, at Step S306, if the volume data is "XY<Z" (No at Step S306), the reconstructing circuitry 1352 causes the rendering processing circuitry 136 to perform a rendering operation with the sense of depth of the reconstructed volume data adjusted. Specifically, the rendering processing circuitry 136 generates a stereoscopic image (parallax image group) with the sense of depth adjusted by using the volume data that is reconstructed by the reconstructing circuitry 1352 (Step S309), and the display control circuitry 1353 causes the display 132 to display the stereoscopic image that is generated by the rendering processing circuitry 136 (Step S308).

As described above, according to the third embodiment, in accordance with the size of the medical image data that is acquired by the image-information acquiring circuitry 1351, the reconstructing circuitry 1352 enlarges or reduces the stereoscopic image that is generated from the medical image data. Therefore, the workstation 130 according to the third embodiment makes it possible to display a stereoscopic image whose appearance has been adjusted.

Furthermore, according to the third embodiment, the reconstructing circuitry 1352 enlarges or reduces the stereoscopic image in the depth direction in accordance with the size of the medical image data in the depth direction, acquired by the image-information acquiring circuitry 1351. Therefore, the workstation 130 according to the third embodiment may match the degrees of protrusion of stereoscopic images and may display more easily observable medical images in a stable manner.

Fourth Embodiment

In the above-described first to third embodiments, an explanation is given of a case where stereoscopic images of multiple types of medical images are displayed, where multimodality is the target. In a fourth embodiment, an explanation is given of a case where the stereoscopic image of a single type of medical image is displayed, where the single modality is the target. As described above, the medical image that is acquired by each modality has a different resolution performance and each has a suitable condition as the condition for generating a parallax image from each medical image. Therefore, the workstation 130 according to the fourth embodiment sets the condition in accordance with the type of medical-image diagnostic apparatus, thereby displaying an easily observable medical image in a stable manner. Here, compared with the first to third embodiments, the information that is stored in the storage circuitry 134 and the type of operation of the reconstructing circuitry 1352 are different in the workstation 130 according to the fourth embodiment. An explanation is primarily given below of this.

The storage circuitry 134 stores the condition for generating a parallax image group for each type of medical-image diagnostic apparatus. FIG. 20A and FIG. 20B are diagrams that illustrate examples of the information that is stored in the storage circuitry 134 according to the fourth embodiment. For example, as illustrated in FIG. 20A, the storage circuitry 134 stores the modality information that relates modality, type, area, and degree of protrusion. Here, "modality", illustrated in FIG. 20A, indicates the type of medical-image diagnostic apparatus that acquires a medical image. Furthermore, "type", illustrated in FIG. 20A, indicates the site, for which the medical image is acquired, and the type of examination. Furthermore, "area", illustrated in FIG. 20A, indicates the percentage which the area, specified in volume data, falls within. Here, "AP (Anterior-Posterior)", which is related to "area", indicates the anteriority and posteriority with the front side of the subject as a reference, and "RL (Right-Left)" indicates the right and left. Furthermore, "degree of protrusion", illustrated in FIG. 20A, indicates the percentage of the maximum protrusion degree.

For example, as illustrated in FIG. 20A, the storage circuitry 134 stores "type: head CTA, area AP: 100%, area RL: 100%, degree of protrusion: 100%" that is related to "modality: CT". This information indicates that the CT image, captured by an X-ray CT apparatus during the CTA for the head, is generated such that the area in the anterior-posterior direction falls within 100% of the maximum protrusion degree, the area in the right-and-left direction falls within 100% of the maximum protrusion degree, and the degree of protrusion becomes 100% of the maximum protrusion degree. For example, if the maximum protrusion degree of the stereoscopic display monitor is "4 cm", it means that the volume data falls within "4 cm" in the anterior-posterior direction and falls within "4 cm" in the right-and-left direction and the degree of protrusion is "4 cm".

For example, in the case of the CTA for the head, the resolution performance is high, and the size of the target site does not much differ in the anterior-posterior direction and in the right-and-left direction. Therefore, if the degree of protrusion is the maximum protrusion degree of "4 cm", there is no possibility of deterioration of the image quality. Furthermore, as the size of the target site does not much differ in the anterior-posterior direction and in the right-and-left direction, even if it falls within "4 cm" in the anterior-posterior direction and in the right-and-left direction, improper decompression or compression does not occur in the image. Therefore, for example, in the case of the CTA for the head, the above-described condition is set. Conversely, in the case of "modality: CT, type: chest simple", the size of the target site in the anterior-posterior direction is smaller compared to the right-and-left direction; therefore, to prevent the occurrence of improper decompression, "area AP: 50%" is set. In the same manner, the storage circuitry 134 stores the type, the area, and the degree of protrusion in a related manner with regard to MRI or the nuclear (PET, SPECT).

Furthermore, as illustrated in FIG. 20B, the storage circuitry 134 stores the relation information in which the degree of protrusion is related to the parallactic angle for each pixel. For example, the storage circuitry 134 stores "degree of protrusion: 100%, parallactic angle: 0.4 degrees" that is related to the pixels "512×512". This information means that, for the medical image that is acquired with the pixels "512×512", if the degree of protrusion is "100%", the parallactic angle is "0.4 degrees". For example, an example is such that, if the maximum protrusion degree of the stereoscopic display monitor is "4 cm", it means that the parallactic angle is "0.4 degrees" so that the degree of protrusion of the medical image, acquired with the pixels "512×512", is "4 cm".

The reconstructing circuitry 1352 receives, from the image-information acquiring circuitry 1351, the image information on the medical image for generating a parallax image group and, based on the received image information, refers to the modality information that is illustrated in FIG. 20A and the relation information that is illustrated in FIG. 20B, thereby setting the conditions for generating the parallax image group. For example, in the case of the maximum protrusion degree of "4 cm" and the head CTA volume data that is acquired with the pixels "512×512", the reconstructing circuitry 1352 refers to the modality information of FIG. 20A and determines that the area in the volume data falls within "4 cm" and the degree of protrusion is "4 cm". Then, the reconstructing circuitry 1352 refers to the relation information of FIG. 20B and determines that the parallactic angle is "0.4 degrees" so that the degree of protrusion of the medical image, acquired with the pixels "512×512", is "4 cm (100%)".

The reconstructing circuitry 1352 sets the condition for each type of modality as described above and causes the rendering processing circuitry 136 to perform a volume rendering operation. The display control circuitry 1353 causes the display 132, which is the stereoscopic display monitor, to display the parallax image group that is generated under the condition, which is set by the reconstructing circuitry 1352.

Fifth Embodiment

Although the first to fourth embodiments have been described above, various different embodiments may be implemented other than the above-described first to fourth embodiments.

In the above-described embodiments, an explanation is given of a case where the workstation 130 displays a stereoscopic image. However, this is not a limitation on the embodiment, and there may be a case where it is displayed on, for example, the medical-image diagnostic apparatus 110 or the terminal apparatus 140. In such a case, the medical-image diagnostic apparatus 110 or the terminal apparatus 140 includes each of the functional circuitry that are illustrated in FIG. 8.

Furthermore, in the above-described embodiments, an explanation is given of a case where the resolution to be reconstructed, or the like, is determined on the basis of the image information on the volume data for displaying the stereoscopic image. However, this is not a limitation on the embodiment, and there may be a case where, for example, the resolution to be reconstructed, or the like, is previously preset and is manually adjusted as appropriate. In such a case, there may be a case where it is previously preset such that the volume data is output with a predetermined resolution in each of the medical-image diagnostic apparatus 110, or it is preset in the medical-image diagnostic apparatus 110 that displays stereoscopic images.

Furthermore, in the above-described embodiments, an explanation is given of a case where reconstruction is conducted on volume data that is acquired by multiple types of medical-image diagnostic apparatus. However, this is not a limitation on the embodiment and, for example, there may be a case where reconstruction is conducted on the volume data that is acquired by the same medical-image diagnostic apparatus with different resolutions.

Furthermore, in the above-described embodiments, an explanation is given of a case where the terminal apparatus 140 displays, or the like, the medical image, or the like, which is acquired from the image storage apparatus 120. However, this is not a limitation on the embodiment, and there may be a case where, for example, the terminal apparatus 140 is directly connected to the medical-image diagnostic apparatus 110 or the workstation 130.

Furthermore, the configuration of the workstation 130 as the medical-image display apparatus according to the above-described first to third embodiments is only an example, and integration and separation of each circuitry may be conducted as appropriate. For example, the image-information acquiring circuitry 1351 and the reconstructing circuitry 1352 may be integrated, or the reconstructing circuitry 1352 may be separated into a volume-data reconstructing circuitry that reconstructs volume data and a rendering control circuitry that controls the rendering processing circuitry.

Furthermore, the functions of the image-information acquiring circuitry 1351, the reconstructing circuitry 1352, and the display control circuitry 1353, which are explained in the first embodiment to the third embodiment, may be implemented by software. For example, the functions of the image-information acquiring circuitry 1351, the reconstructing circuitry 1352, and the display control circuitry 1353 are implemented by executing, on a computer, a medical-image display program that defines the steps of the operations that are performed by the image-information acquiring circuitry 1351, the reconstructing circuitry 1352, and the display control circuitry 1353 as explained in the above embodiments. The medical-image display program is stored in, for example, a hard disk or a semiconductor memory device, and it is read and executed by a processor, such as CPU or MPU. Furthermore, the medical-image display program may be distributed by being recorded in a recording medium readable by a computer, such as a CD-ROM (Compact Disc-Read Only Memory), MO (Magnetic Optical disk), or DVD (Digital Versatile Disc).

As described above, according to the embodiment, the medical-image processing apparatus according to the present embodiment makes it possible to display easily observable medical images in a stable manner.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical-image processing apparatus comprising:
   processing circuitry configured to
   perform a volume rendering process on volume data while moving a viewpoint position by a predetermined parallactic angle, thereby generating a parallax image group that includes a plurality of parallax images with the different viewpoint positions, and
   display the parallax image group as a stereoscopic image on a stereoscopic display monitor, wherein
   with regard to volume data that is acquired by multiple types of medical-image diagnostic apparatus, the processing circuitry is configured to adjust each of the parallactic angles during generation of the parallax image group according to a difference of resolution among a plurality of volume data and, in accordance with each of the adjusted parallactic angles, generate each parallax image group based on volume data that is acquired by each of the multiple types of the medical-image diagnostic apparatus.

2. The medical-image processing apparatus according to claim 1, wherein, with regard to volume data that is acquired by each of the multiple types of the medical-image diagnostic apparatus, the processing circuitry is configured to adjust each of the parallactic angles during generation of the parallax image group such that a degree of protrusion during display on the stereoscopic display monitor is matched, and generate each parallax image group based on volume data that is acquired by each of the multiple types of the medical-image diagnostic apparatus in accordance with each of the adjusted parallactic angles.

3. The medical-image processing apparatus according to claim 1, wherein, with regard to volume data that is acquired by each of the multiple types of the medical-image diagnostic apparatus, the processing circuitry is configured to adjust each of the parallactic angles during generation of the parallax image group in accordance with a resolution performance in a direction that corresponds to a screen direction during display on the stereoscopic display monitor and generate each parallax image group based on volume data that is acquired by each of the multiple types of the medical-image diagnostic apparatus in accordance with each of the adjusted parallactic angles.

4. The medical-image processing apparatus according to claim 1, wherein the processing circuitry is configured to cause the stereoscopic display monitor to display a fusion image that is a fusion of a plurality of parallax image groups that are generated.

5. The medical-image processing apparatus according to claim 4, wherein
   the processing circuitry is configured to
   allocate volume data, acquired by each of the multiple types of the medical-image diagnostic apparatus, in a first position and a second position of a virtual space, perform a volume rendering process in a state such that each positional information is retained, and generate a plurality of parallax image groups based on each volume data, and
   cause the stereoscopic display monitor to display a plurality of parallax image groups that are generated, thereby displaying a stereoscopic image where fusion images are allocated in positions that correspond to the first position and the second position in a depth direction of the stereoscopic display monitor.

6. The medical-image processing apparatus according to claim 1, wherein the processing circuitry is configured to select specific volume data among volume data that is acquired by each of the multiple types of the medical-image diagnostic apparatus and individually set a parallactic angle that corresponds to the selected volume data.

7. The medical-image processing apparatus according to claim 1, wherein the processing circuitry is configured to adjust the parallactic angle in accordance with a maximum protrusion degree of the stereoscopic display monitor.

8. The medical-image processing apparatus according to claim 1, wherein the processing circuitry is configured to
   select specific volume data among volume data that is acquired by each of the multiple types of the medical-image diagnostic apparatus, and
   change a protrusion position of the specific volume data.

9. The medical-image processing apparatus according to claim 1, wherein the processing circuitry is configured to adjust each of the parallactic angles during generation of the parallax image group in accordance with a highest resolution performance among each resolution performance of volume data that is acquired by each of the multiple types of the medical-image diagnostic apparatus, and generate each parallax image group based on volume data that is acquired by each of the multiple types of the medical-image diagnostic apparatus in accordance with each of the adjusted parallactic angle.

10. A medical-image processing apparatus comprising:
processing circuitry configured to
perform a volume rendering operation on volume data while moving a viewpoint position by a predetermined parallactic angle, thereby generating a parallax image group that includes a plurality of parallax images with the different viewpoint positions,
set the parallactic angle based on resolution of the volume data, the resolution changing according to a type of medical-image diagnostic apparatus of the volume data, and
display the parallax image group as a stereoscopic image on a stereoscopic display monitor, wherein
the processing circuitry is configured to generate a parallax image group based on the volume data in accordance with the set parallactic angle.

11. The medical-image processing apparatus according to claim 10, wherein the processing circuitry is configured to set the parallactic angle based on the type of modality and a capturing site of the volume data.

12. The medical-image processing apparatus according to claim 1, wherein the processing circuitry is configured to cause the stereoscopic display monitor to display a model image that corresponds to the parallax image group on a front side or a back side of the parallax image group.

13. The medical-image processing apparatus according to claim 10, wherein the processing circuitry is configured to cause the stereoscopic display monitor to display a model image that corresponds to the parallax image group on a front side or a back side of the parallax image group.

14. The medical-image processing apparatus according to claim 1, wherein the processing circuitry is configured to generate the parallax image group in accordance with a resolution performance of each volume data that is acquired by each of the multiple types of the medical-image diagnostic apparatus and a screen resolution performance of the stereoscopic display monitor.

15. The medical-image processing apparatus according to claim 10, wherein the processing circuitry is configured to generate the parallax image group in accordance with a resolution performance of each volume data that is acquired by each of the multiple types of the medical-image diagnostic apparatus and a screen resolution performance of the stereoscopic display monitor.

16. The medical-image processing apparatus according to claim 1, wherein the processing circuitry is configured to cause the stereoscopic display monitor to display the stereoscopic image in an actual size.

17. The medical-image processing apparatus according to claim 10, wherein the processing circuitry is configured to cause the stereoscopic display monitor to display the stereoscopic image in an actual size.

* * * * *